United States Patent
Dickman et al.

(10) Patent No.: US 10,106,811 B2
(45) Date of Patent: Oct. 23, 2018

(54) COMPOSITIONS, ORGANISMS, SYSTEMS, AND METHODS FOR ALTERING COLD, DROUGHT, AND SALT TOLERANCE IN PLANTS

(71) Applicant: THE TEXAS A & M UNIVERSITY SYSTEM, College Station, TX (US)

(72) Inventors: Martin B. Dickman, College Station, TX (US); T. Erik Mirkov, Harlingen, TX (US); Getu Beyene, St. Louis, MO (US); Mayra Faion-Molina, Sao Paulo (BR); Marco David Molina Risco, College Station, TX (US)

(73) Assignee: The Texas A&M University System, College Station, TX (US)

( * ) Notice: Subject to any disclaimer, the term of this patent is extended or adjusted under 35 U.S.C. 154(b) by 360 days.

(21) Appl. No.: 14/213,650

(22) Filed: Mar. 14, 2014

(65) Prior Publication Data
US 2014/0283202 A1    Sep. 18, 2014

Related U.S. Application Data

(60) Provisional application No. 61/852,242, filed on Mar. 15, 2013.

(51) Int. Cl.
*C12N 15/82* (2006.01)
*C07K 14/415* (2006.01)

(52) U.S. Cl.
CPC ........ *C12N 15/8271* (2013.01); *C07K 14/415* (2013.01); *C12N 15/8261* (2013.01); *C12N 15/8273* (2013.01); *Y02A 40/146* (2018.01)

(58) Field of Classification Search
None
See application file for complete search history.

(56) References Cited

U.S. PATENT DOCUMENTS

2003/0005480 A1    1/2003 Ohashi et al.

FOREIGN PATENT DOCUMENTS

WO    WO 2008/119136 A1 * 10/2008

OTHER PUBLICATIONS

Doukhanina et al., 2006, The Journal of Biological Chemistry 281: 18793-18801.*
Rana et al., 2012, African Journal of Biotechnology 11: 88-99.*
Cramer et al., 2011, BMC Plant Biology 11:163.*
Smouni et al., 2002, Funct. Plant Biol. 29: 649-656.*
Zhang et al., 2007, Sugarcane. In: Transgenic Crops V; Biotechnology in Agriculture and Forestry, vol. 60, Springer-Verlag, pp. 537-551.*
Beyene, G., et al., "Unprecedented enhancement of transient gene expression from minimal cassettes using a double terminator," Plant Cell Rep, (2011), 30, pp. 13-25.
NCBI, GenBank acession No. NP_190746.2, "BCL-2-associated athanogene 4 [*Arabidopsis thaliana*]," previous version dated May 28, 2011, updated Jan. 22, 2014, 2 pages.
NCBI, GenBank acession No. NP_499284.1, "Protein CED-9 [Caenorhabditis elegans]," dated Feb. 28, 2013, 2 pages.
International Search Report and Written Opinion, PCT/US2014/029135, dated Aug. 26, 2014, 20 pages.
NCBI, GenBank acession No. NP_000624.2, "apoptosis regulator Bcl-2 alpha isoform [*Homo sapiens*]," previous version dated Jan. 28, 2013, updated May 18, 2014, 4 pages.
Larkin, M.A., et al., "Clustal W and Clustal X version 2.0," Bioinformatics Applications Note, vol. 23, No. 21, (2007), pp. 2947-2948.
Li, W., et al., "Abiotic stress induces apoptotic-like features in tobacco that is inhibited by expression of human Bcl-2," Biotechnology Letters, vol. 26, (2004), pp. 87-95.
Doukhanina, E.V., et al., "Identification and Functional Characterization of the BAG Protein Family in *Arabidopsis thaliana*," The Journal of Biological Chemistry, vol. 281, No. 27, pp. 18793-18801, Jul. 7, 2006.
Joyce, P., et al., "Selection system and co-cultivation medium are important determinants of Agrobacterium-mediated transformation of sugarcane," Plant Cell Rep, (2010), vol. 29, pp. 173-183.
Nuin, P.A.S., et al., "The accuracy of several multiple sequence alignment programs for proteins," BMC Bioinformatics, (2006), vol. 7, pp. 1-18.
Pearson, W.R., "Rapid and Sensitive Sequence Comparison with FASTP and FASTA," Rapid Sequence Comparison, Methods in Enzymology, vol. 183, (1990), 36 pages.
Pearson, W.R., et al., "Improved tools for biological sequence comparison," Proc. Natl. Acad. Sci., vol. 85, (Apr. 1988), vol. 85, pp. 2444-2448.
Gallo-Meagher, M., et al., "Herbicde Resistant Transgenic Sugarcane Plants Containing the bar Gene," Crop Sci., vol. 36, (1996), pp. 1367-1374.
Gallo-Meagher, M., et al., "Effects in tissue type and promoter strength on transient GUS expression in sugarcane following particle bombardment," Plant Cell Reports (1993), vol. 23, pp. 666-670.

* cited by examiner

*Primary Examiner* — Matthew R Keogh
*Assistant Examiner* — Bratislav Stankovic
(74) *Attorney, Agent, or Firm* — Dentons US LLP

(57) ABSTRACT

The present disclosure relates, in some embodiments, to materials, systems, organisms, and methods for enhancing abiotic stress tolerance (e.g., cold, salinity, drought, heat, wind) and/or enhancing biomass in plants. For example, enhancing abiotic stress tolerance may be achieved in plants having *Arabidopsis thaliana* BCL-2-associated athanogene 4 (AtBAG4) nucleic acids and/or polypeptides, *Caenorhabditis elegans* Ced-9 nucleic acids and/or polypeptides, and/or human Bcl-2-161 nucleic acids and/or polypeptides.

12 Claims, 18 Drawing Sheets
Specification includes a Sequence Listing.

FIRST DROUGHT STRESS | SECOND DROUGHT STRESS
CONTROL  TRANSGENIC LINES | CONTROL  TRANSGENIC LINES

CONTROL  TRANSGENIC LINES

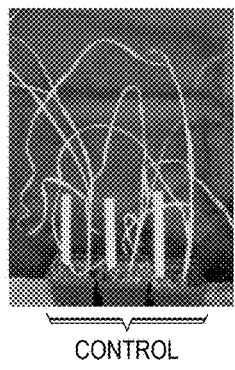 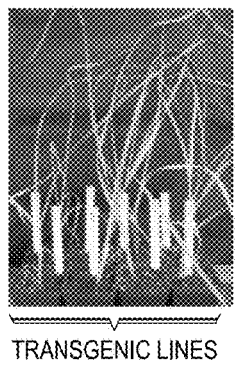 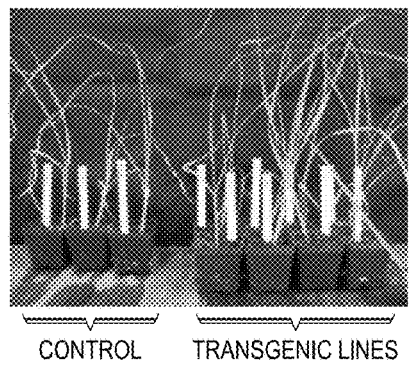
FIG. 11A  FIG. 11B  FIG. 11C
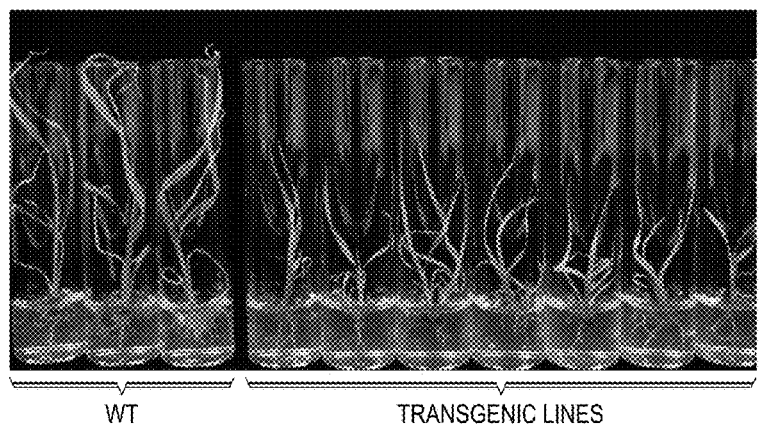
FIG. 12
 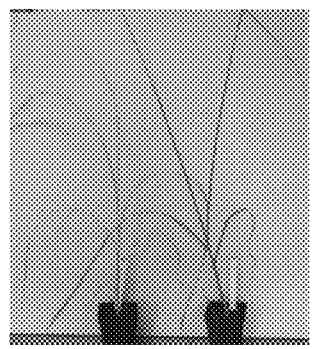
FIG. 13A  FIG. 13B

WT    TRANSGENIC LINES

WT    TRANSGENIC LINES

WT    TRANSGENIC LINES

SEQUENCE LISTING

```
<160> NUMBER OF SEQ ID NOS: 10

<210> SEQ ID NO 1
<211> LENGTH: 1203
<212> TYPE: DNA
<213> ORGANISM: Arabidopsis thaliana

<400> SEQUENCE: 1
aggagaattt gtatgttttg aggaggtgtg catcatccgt ctatcaatac cctgacaagg      60
aaaaccctaa ttttttttgg cccaaagggt tttatacttt aatctcatac tccgattcat     120
tgtcgaaaaa cgatgatgca taattcaacc gaagaatcgg aatgggaggt gagacctggt     180
ggtatgctcg tccaacgaag agacgacgcc gcttcctccg accacaaacc tctccaggat     240
cccgactctg cttccgccgc ttttgctcaa accatcagaa tcactgtttc tcatggctca     300
tcgcaccacg atcttcatat ttctgctcac gccactttcg gggatgtgaa gaaagctctt     360
gttcagaaaa ctggattgga agctagtgaa ttgaagatct tgttcagagg agttgagaga     420
gatgatgctg aacaattgca agctgctggt gttaaggatg cgtctaagct tgttgttgtt     480
gttgaggata cgaataagag agtggaacaa cagcctcctg tggtaactaa agagatggaa     540
aaagctattg ctgctgttaa cgcggttaca ggagaggtcg ataagctctc ggatagagtt     600
gttgctttag aagttgctgt gaatggaggg acgcaagttg cggtgcggga gtttgacatg     660
gctgcagagc ttcttatgag gcagctgctc aaattggatg gcattgaggc tgaagggac      720 gctaaagtac agcgtaaggc tgaggtacgt agaatccaaa acttgcagga ggctgtggat     780
aagttgaagg caagatgttc aaatccgttt gtggatcaga gcaaagctgc agctgtaagc     840
actgagtggg aatcgttcgg aaacggtgtc ggaagcttga acctcctcc gccagcttcg     900 ccttcggcca atgtaactca agattgggag aaatttgact gacattttag tactgctacg     960
ttgccttgga aaaaatgct tattgaaact gtttatcttt ttgattattg ttaaatattg    1020
gaaaacgacc atcgtcttta tcttctaatg tatagatata ttatatatag tatcggaaat    1080
ctacatctct gtacgttatg ttggaataat ccctgggaat agtctttgat gtctctcagt    1140
```

```
ctctgtcgtg cctaattggc ttatgtcgta gtactaaaga ttatggctac gagttttgga    1200
gac                                                                  1203
```

<210> SEQ ID NO 2
<211> LENGTH: 269
<212> TYPE: PRT
<213> ORGANISM: Arabidopsis thaliana

<400> SEQUENCE: 2

```
Met Met His Asn Ser Thr Glu Glu Ser Glu Trp Glu Val Arg Pro Gly
1               5                  10                  15

Gly Met Leu Val Gln Arg Arg Asp Asp Ala Ala Ser Ser Asp His Lys
            20                  25                  30

Pro Leu Gln Asp Pro Asp Ser Ala Ser Ala Ala Phe Ala Gln Thr Ile
        35                  40                  45

Arg Ile Thr Val Ser His Gly Ser Ser His His Asp Leu His Ile Ser
    50                  55                  60

Ala His Ala Thr Phe Gly Asp Val Lys Lys Ala Leu Val Gln Lys Thr
65                  70                  75                  80

Gly Leu Glu Ala Ser Glu Leu Lys Ile Leu Phe Arg Gly Val Glu Arg
                85                  90                  95

Asp Asp Ala Glu Gln Leu Gln Ala Ala Gly Val Lys Asp Ala Ser Lys
            100                 105                 110

Leu Val Val Val Val Glu Asp Thr Asn Lys Arg Val Glu Gln Gln Pro
        115                 120                 125

Pro Val Val Thr Lys Glu Met Glu Lys Ala Ile Ala Ala Val Asn Ala
    130                 135                 140

Val Thr Gly Glu Val Asp Lys Leu Ser Asp Arg Val Val Ala Leu Glu
145                 150                 155                 160

Val Ala Val Asn Gly Gly Thr Gln Val Ala Val Arg Glu Phe Asp Met
                165                 170                 175

Ala Ala Glu Leu Leu Met Arg Gln Leu Leu Lys Leu Asp Gly Ile Glu
            180                 185                 190

Ala Glu Gly Asp Ala Lys Val Gln Arg Lys Ala Glu Val Arg Arg Ile
        195                 200                 205

Gln Asn Leu Gln Glu Ala Val Asp Lys Leu Lys Ala Arg Cys Ser Asn
    210                 215                 220

Pro Phe Val Asp Gln Ser Lys Ala Ala Ala Val Ser Thr Glu Trp Glu
225                 230                 235                 240

Ser Phe Gly Asn Gly Val Gly Ser Leu Asn Pro Pro Pro Ala Ser
                245                 250                 255

Pro Ser Ala Asn Val Thr Gln Asp Trp Glu Lys Phe Asp
            260                 265
```

<210> SEQ ID NO 3
<211> LENGTH: 1909
<212> TYPE: DNA
<213> ORGANISM: Caenorhabditis elegans

<400> SEQUENCE: 3

```
atgacacgct gcacggcgga caactcgctg acgaatccgg cgtatcggcg acgaacgatg     60
gcgactggcg agatgaagga gtttctgggg ataaaaggca cagagcccac cgattttgga    120
atcaatagtg atgctcagga cttgccatca ccgagtaggc aggcttcgac gcgaagaatg    180
tccatcggag agtcaattga tggaaaaatc aatgattggg aagagccaag gcttgatatc    240
```

```
gagggatttg tggtaatttt ttaattttt tttgtaaata aaatttcctg ctgcttccag      300
gtcgactatt tcacgcaccg aatccggcaa acggaatgg aatggtttgg agcaccggga      360
ttgccgtgtg gagtgcaacc ggagcacgaa atgatgcgag ttatgggaac gatattcgag      420
aagaagcacg cggaaaattt tgagaccttc tgtgagcagc tgctcgcagt gcccagaatc      480
tcattttcac tgtatcagga tgtggttcgg acggttggaa atgcacagac agatcaatgt      540
ccaatgtctt atggacgttt ggtaagggag aaaatactga aaaaaagttt gcaaaaattc      600
gaaaattcgc cagaaaggtg gcagaaaaaa catttgcaaa aattgtttgt tttccttcag      660
gaaatcagca aaacttggtc aaaaatagcc aattatgtg tcttttttga agttttcca      720
ttaaaaaacc acgaattttg atcccggatt gtaattttt ttgttgataa attagcagaa      780
aactttacga attcgattaa aaacgttatt ttctattcga atatttttaa agcatatttt      840
ccttgatttg tatttgcgaa aaagatctgc tgatttatca aaaatcggtt tttaaatgta      900
aaatttgtgg aaaatacatt aaaattcgat ttttgaactt ttttcttcga aaaacaggtt      960
tttctgctga tttgctgaac gaaaaacccc aaaaattcaa ttttcgaaca ttaaaaacca     1020
gaaaaatcgt ttttttaagc ttaattttcc gccagaaatg aacgaattaa attgcaaatt     1080
tctaattttc agataggtct aatctcgttc ggcggtttcg tagctgcaaa atgatggaa      1140
tccgtggaac tgcagggaca agtgcgaaac ctcttcgttt acacatcgct gttcatcaaa     1200
acgcggatcc gcaacaactg gaaggaacac aatcggagct gggtaaggag tatttgcata     1260
gacattagaa gtcaatatcc cccttttccct agtaccttg acttcccggg gtgttggtaa     1320
gccgataatt acagggttcg gtagcctctt gggggacag ctggaaacat attcaagtat      1380
attactgttt atgataatgt tattgttacg ggaatacaaa attcgcagaa tgcgtatttc     1440
acaacatatt tgacgcgcaa aatatccagt agagaaaact acagtaattc tttaaatttt     1500
taaaattttt acaattaaag aaaataacca ctaatcaaaa gaattaatt tcaaaaatcg      1560
agcccgtaaa tcgactacag taggcattta aagaattact gtagttttcg ctacgagata     1620
tttccgcctc aaatatgttg tgaaatacgc attcacggat ttttgtgttc cccggaatat     1680
gctctaaagc attatttgtg aaaataaaaa atcaagaaaa aaattgcagg acgacttcat     1740
gacactcgga aaacaaatga agaggacta cgaacgagca gaagctgaaa agtgggacg       1800
ccggaagcag aacagacggt ggtcgatgat tggcgctgga gtaacagctg gagccattgg     1860
aatcgttgga gtcgtcgtgt gtgggcggat gatgttcagc ttgaagtaa                1909
```

<210> SEQ ID NO 4
<211> LENGTH: 280
<212> TYPE: PRT
<213> ORGANISM: Caenorhabditis elegans

<400> SEQUENCE: 4

Met Thr Arg Cys Thr Ala Asp Asn Ser Leu Thr Asn Pro Ala Tyr Arg
1               5                   10                  15

Arg Arg Thr Met Ala Thr Gly Glu Met Lys Glu Phe Leu Gly Ile Lys
                20                  25                  30

Gly Thr Glu Pro Thr Asp Phe Gly Ile Asn Ser Asp Ala Gln Asp Leu
            35                  40                  45

Pro Ser Pro Ser Arg Gln Ala Ser Thr Arg Arg Met Ser Ile Gly Glu
        50                  55                  60

Ser Ile Asp Gly Lys Ile Asn Asp Trp Glu Glu Pro Arg Leu Asp Ile
65                  70                  75                  80

```
Glu Gly Phe Val Val Asp Tyr Phe Thr His Arg Ile Arg Gln Asn Gly
                85                  90                  95
Met Glu Trp Phe Gly Ala Pro Gly Leu Pro Cys Gly Val Gln Pro Glu
            100                 105                 110
His Glu Met Met Arg Val Met Gly Thr Ile Phe Glu Lys Lys His Ala
        115                 120                 125
Glu Asn Phe Glu Thr Phe Cys Glu Gln Leu Leu Ala Val Pro Arg Ile
    130                 135                 140
Ser Phe Ser Leu Tyr Gln Asp Val Val Arg Thr Val Gly Asn Ala Gln
145                 150                 155                 160
Thr Asp Gln Cys Pro Met Ser Tyr Gly Arg Leu Ile Gly Leu Ile Ser
                165                 170                 175
Phe Gly Gly Phe Val Ala Ala Lys Met Met Glu Ser Val Glu Leu Gln
            180                 185                 190
Gly Gln Val Arg Asn Leu Phe Val Tyr Thr Ser Leu Phe Ile Lys Thr
        195                 200                 205
Arg Ile Arg Asn Asn Trp Lys Glu His Asn Arg Ser Trp Asp Asp Phe
    210                 215                 220
Met Thr Leu Gly Lys Gln Met Lys Glu Asp Tyr Glu Arg Ala Glu Ala
225                 230                 235                 240
Glu Lys Val Gly Arg Arg Lys Gln Asn Arg Arg Trp Ser Met Ile Gly
                245                 250                 255
Ala Gly Val Thr Ala Gly Ala Ile Gly Ile Val Gly Val Val Val Cys
            260                 265                 270
Gly Arg Met Met Phe Ser Leu Lys
        275                 280

<210> SEQ ID NO 5
<211> LENGTH: 3215
<212> TYPE: DNA
<213> ORGANISM: Artificial Sequence
<220> FEATURE:
<223> OTHER INFORMATION: Ubi-Ced9-35ST (pTEM09) vector for biolostic
      bombardment.
<220> FEATURE:
<221> NAME/KEY: Expression cassette
<222> LOCATION: (1)..(3215)
<220> FEATURE:
<221> NAME/KEY: Ubi promoter, first exon and intron
<222> LOCATION: (1)..(1992)
<220> FEATURE:
<221> NAME/KEY: TEV translation enhancer
<222> LOCATION: (1998)..(2134)
<220> FEATURE:
<221> NAME/KEY: Ced9 CDS
<222> LOCATION: (2135)..(2980)
<220> FEATURE:
<221> NAME/KEY: 35S terminator
<222> LOCATION: (2981)..(3215)

<400> SEQUENCE: 5
tgcagtgcag cgtgacccgg tcgtgcccct ctctagagat aatgagcatt gcatgtctaa      60
gttataaaaa attaccacat attttttttg tcacacttgt ttgaagtgca gtttatctat     120
ctttatacat atatttaaac tttactctac gaataatata atctatagta ctacaataat     180
atcagtgttt tagagaatca tataaatgaa cagttagaca tggtctaaag gacaattgag     240
tattttgaca acaggactct acagtttat cttttagtg tgcatgtgtt ctccttttt       300 tttgcaaata gcttcaccta tataatactt catccatttt attagtacat ccatttaggg     360
tttagggtta atggttttta tagactaatt tttttagtac atctattta ttctatttta     420
```

| | | | | |
|---|---|---|---|---|
| gcctctaaat | taagaaaact | aaaactctat | tttagttttt | ttatttaata atttagatat | 480 |
| aaaatagaat | aaaataaagt | gactaaaaat | taaacaaata | cccttttaaga aattaaaaaa | 540 |
| actaaggaaa | cattttttctt | gtttcgagta | gataatgcca | gcctgttaaa cgccgtcgac | 600 |
| gagtctaacg | gacaccaacc | agcgaaccag | cagcgtcgcg | tcgggccaag cgaagcagac | 660 |
| ggcacggcat | ctctgtcgct | gcctctggac | ccctctcgag | agttccgctc caccgttgga | 720 |
| cttgctccgc | tgtcggcatc | cagaaattgc | gtggcggagc | ggcagacgtg agccggcacg | 780 |
| gcaggcggcc | tcctcctcct | ctcacggcac | cggcagctac | gggggattcc tttcccaccg | 840 |
| ctccttcgct | ttcccttcct | cgcccgccgt | aataaataga | caccccctcc cacccctctt | 900 |
| tccccaacct | cgtgttgttc | ggagcgcaca | cacacacaac | cagatctccc ccaaatccac | 960 |
| ccgtcggcac | ctccgcttca | aggtacgccg | ctcgtcctcc | cccccccccc ctctctacct | 1020 |
| tctctagatc | ggcgttccgg | tccatggtta | gggcccggta | gttctacttc tgttcatgtt | 1080 |
| tgtgttagat | ccgtgtttgt | gttagatccg | tgctgctagc | gttcgtacac ggatgcgacc | 1140 |
| tgtacgtcag | acacgttctg | attgctaact | tgccagtgtt | tctctttggg gaatcctggg | 1200 |
| atggctctag | ccgttccgca | gacgggatcg | atttcatgat | ttttttttgtt tcgttgcata | 1260 |
| gggtttggtt | tgccctttttc | ctttatttca | atatatgccg | tgcacttgtt tgtcgggtca | 1320 |
| tcttttcatg | ctttttttttg | tcttggttgt | gatgatgtgg | tctggttggg cggtcgttct | 1380 |
| agatcggagt | agaattctgt | ttcaaactac | ctggtggatt | tattaattttt ggatctgtat | 1440 |
| gtgtgtgcca | tacatattca | tagttacgaa | ttgaagatga | tggatggaaa tatcgatcta | 1500 |
| ggataggtat | acatgttgat | gcgggttttta | ctgatgcata | tacagagatg ctttttgttc | 1560 |
| gcttggttgt | gatgatgtgg | tgtggttggg | cggtcgttca | ttcgttctag atcggagtag | 1620 |
| aatactgttt | caaactacct | ggtgtattta | ttaattttgg | aactgtatgt gtgtgtcata | 1680 |
| catcttcata | gttacgagtt | taagatggat | ggaaatatcg | atctaggata ggtatacatg | 1740 |
| ttgatgtggg | ttttactgat | gcatatacat | gatggcatat | gcagcatcta ttcatatgct | 1800 |
| ctaaccttga | gtacctatct | attataataa | acaagtatgt | tttataatta ttttgatctt | 1860 |
| gatatacttg | gatgatggca | tatgcagcag | ctatatgtgg | atttttttag ccctgccttc | 1920 |
| atacgctatt | tatttgcttg | gtactgtttc | ttttgtcgat | gctcaccctg ttgtttggtg | 1980 |
| ttacttctgc | aggtcgagaa | ttctcaacac | aacatataca | aaacaaacga atctcaagca | 2040 |
| atcaagcatt | ctacttctat | tgcagcaatt | taaatcattt | cttttaaagc aaaagcaatt | 2100 |
| ttctgaaaat | tttcaccatt | tacgaacgat | agccatggcg | acacgctgca cggcggacaa | 2160 |
| ctcgctgacg | aatccggcgt | atcggcgacg | aacgatggcg | actggcgaga tgaaggagtt | 2220 |
| tctgggcata | aaaggcacag | agcccaccga | ttttggaatc | aatagtgatg ctcaggactt | 2280 |
| gccatcaccg | agtaggcagg | cttcgacgcg | aagaatgtcc | atcggagagt caattgatgg | 2340 |
| aaaaatcaat | gattgggaag | agccaaggct | tgatatcgag | ggatttgtgg tcgactattt | 2400 |
| cacgcaccga | atccggcaaa | acggaatgga | atggtttgga | gcaccgggat tgccgtgtgg | 2460 |
| agtgcaaccg | gagcacgaaa | tgatgcgagt | tatgggaacg | atattcgaga agaagcacgc | 2520 |
| ggaaaatttt | gagaccttct | gtgagcagct | gctcgcagtg | cccagaatct cattttcact | 2580 |
| gtatcaggat | gtggttcgga | cggttggaaa | tgcacagaca | gatcaatgtc caatgtctta | 2640 |
| tggacgtttg | ataggtctaa | tctcgttcgg | cggtttcgta | gctgcaaaaa tgatggaatc | 2700 |
| cgtggaactg | cagggacaag | tgcgaaacct | cttcgtttac | acatcgctgt tcatcaaaac | 2760 |

```
gcggatccgc aacaactgga aggaacacaa tcggagctgg gacgacttca tgacactcgg    2820
aaaacaaatg aaagaggact acgaacgagc agaagctgaa aaagtgggac gccggaagca    2880
gaacagacgg tggtcgatga ttggcgctgg agtaacagct ggagccattg gaatcgttgg    2940
agtcgtcgtg tgtgggcgga tgatgttcag cttgaagtaa cgtatttcta gagtccgcaa    3000
aaatcaccag tctctctcta caaatctatc tctctctatt tttctccaga ataatgtgtg    3060
agtagttccc agataaggga attagggttc ttatagggtt tcgctcatgt gttgagcata    3120
taagaaaccc ttagtatgta tttgtatttg taaaatactt ctatcaataa aatttctaat    3180
tcctaaaacc aaaatccagt gacctgcagg catgc                               3215
```

<210> SEQ ID NO 6
<211> LENGTH: 3089
<212> TYPE: DNA
<213> ORGANISM: Artificial Sequence
<220> FEATURE:
<223> OTHER INFORMATION: Ubi-AtBAG4-NOST (pTEM10) vector for biolistic
      bombardment.
<220> FEATURE:
<221> NAME/KEY: Expression cassette
<222> LOCATION: (1)..(3089)
<220> FEATURE:
<221> NAME/KEY: Ubi promoter, first exon and intron
<222> LOCATION: (1)..(1992)
<220> FEATURE:
<221> NAME/KEY: AtBAG4 CDS
<222> LOCATION: (2017)..(2826)
<220> FEATURE:
<221> NAME/KEY: NOS terminator
<222> LOCATION: (2834)..(3089)

<400> SEQUENCE: 6

```
tgcagtgcag cgtgacccgg tcgtgcccct ctctagagat aatgagcatt gcatgtctaa      60
gttataaaaa attaccacat attttttttg tcacacttgt ttgaagtgca gtttatctat     120
ctttatacat atatttaaac tttactctac gaataatata atctatagta ctacaataat     180
atcagtgttt tagagaatca tataaatgaa cagttagaca tggtctaaag gacaattgag     240
tattttgaca acaggactct acagttttat cttttttagtg tgcatgtgtt ctcctttttt     300
tttgcaaata gcttcaccta tataatactt catccatttt attagtacat ccatttaggg     360
tttagggtta atggttttta tagactaatt tttttagtac atctatttta ttctatttta     420
gcctctaaat taagaaaact aaaactctat tttagttttt ttatttaata atttagatat     480
aaaatagaat aaaataaagt gactaaaaat taaacaaata ccctttaaga aattaaaaaa     540
actaaggaaa catttttctt gtttcgagta gataatgcca gcctgttaaa cgccgtcgac     600
gagtctaacg gacaccaacc agcgaaccag cagcgtcgcg tcgggccaag cgaagcagac     660
ggcacggcat ctctgtcgct gcctctggac ccctctcgag agttccgctc caccgttgga     720
cttgctccgc tgtcggcatc cagaaattgc gtggcggagc ggcagacgtg agccggcacg     780
gcaggcggcc tcctcctcct ctcacggcac cggcagctac gggggattcc tttcccaccg     840
ctccttcgct ttcccttcct cgcccgccgt aataaataga caccccctcc acaccctctt     900
tccccaacct cgtgttgttc ggagcgcaca cacacacaac cagatctccc ccaaatccac     960
ccgtcggcac ctccgcttca aggtacgccg ctcgtcctcc cccccccccc ctctctacct    1020
tctctagatc ggcgttccgg tccatggtta gggcccggta gttctacttc tgttcatgtt    1080
tgtgttagat ccgtgtttgt gttagatccg tgctgctagc gttcgtacac ggatgcgacc    1140
tgtacgtcag acacgttctg attgctaact tgccagtgtt tctctttggg gaatcctggg    1200
```

```
atggctctag ccgttccgca gacgggatcg atttcatgat ttttttttgtt tcgttgcata    1260
gggtttggtt tgccctttc ctttatttca atatatgccg tgcacttgtt tgtcgggtca    1320
tcttttcatg ctttttttg tcttggttgt gatgatgtgg tctggttggg cggtcgttct    1380
agatcggagt agaattctgt ttcaaactac ctggtggatt tattaatttt ggatctgtat    1440
gtgtgtgcca tacatattca tagttacgaa ttgaagatga tggatggaaa tatcgatcta    1500
ggataggtat acatgttgat gcgggtttta ctgatgcata tacagagatg ctttttgttc    1560
gcttggttgt gatgatgtgg tgtggttggg cggtcgttca ttcgttctag atcggagtag    1620
aatactgttt caaactacct ggtgtattta ttaattttgg aactgtatgt gtgtgtcata    1680
catcttcata gttacgagtt taagatggat ggaaatatcg atctaggata ggtatacatg    1740
ttgatgtggg ttttactgat gcatatacat gatggcatat gcagcatcta ttcatatgct    1800
ctaaccttga gtacctatct attataataa acaagtatgt tttataatta ttttgatctt    1860
gatatacttg gatgatggca tatgcagcag ctatatgtgg attttttag ccctgccttc    1920
atacgctatt tatttgcttg gtactgtttc ttttgtcgat gctcaccctg ttgtttggtg    1980
ttacttctgc agtgcaggtc gactctagag gatcccatga tgcataattc aaccgaagaa    2040
tcggaatggg aggtgagacc tggtggtatg ctcgtccaac gaagagacga caccgcttcc    2100
tccgaccaca aacctctcca ggatcccgac tctgcttccg ccgcttttgc tcaaaccatc    2160
agaatcactg tttctcatgg ctcatcgcac cacgatcttc atatttctgc tcacgccact    2220
ttcggggatg taaagaaagc tcttgttcag aaaactggat tggaagctag tgaattgaag    2280
atcttgttca gaggagttga gagagatgat gctgaacaat gcaagctgc tggtgttaag    2340
gatgcgtcta agcttgttgt tgttgttgag gatacgaata agagagtgga caacagcct    2400
cctgtggtaa ctaaagagat ggaaaaagct attgctgctg ttaacgcggt tacaggagag    2460
gtcgataagc tctcggatag agttgttgct ttagaagttg ctgtgaatgg agggacgcaa    2520
gttgcggtgc gggagtttga catggctgca gagcttctta tgaggcagct gctcaaattg    2580
gatggcattg aggctgaagg ggacgctaaa gtacagcgta aggctgaggt acgtagaatc    2640
caaaacttgc aggaggctgt ggataagttg aaggcaagat gttcaaatcc gtttgtggat    2700
cagagcaaag ctgcagctgt aagcactgag tgggaatcgt tcggaaacgg tgtcggaagc    2760
ttgaaccctc ctccgccagc ttcgccttcg gccaatgtaa ctcaagattg ggagaaattt    2820
gactgacgag ctcgatcgtt caaacatttg gcaataaagt ttcttaagat tgaatcctgt    2880
tgccggtctt gcgatgatta tcatataatt tctgttgaat tacgttaagc atgtaataat    2940
taacatgtaa tgcatgacgt tatttatgag atgggttttt atgattagag tcccgcaatt    3000
atacatttaa tacgcgatag aaaacaaaat atagcgcgca aactaggata aattatcgcg    3060
cgcggtgtca tctatgttac tagatcgggg                                    3089
```

<210> SEQ ID NO 7
<211> LENGTH: 3316
<212> TYPE: DNA
<213> ORGANISM: Artificial Sequence
<220> FEATURE:
<223> OTHER INFORMATION: Ubi-AtBAG4opt-35S-NOST (pTEM113) codon
      optimized vector fot biolistic bombardment.
<220> FEATURE:
<221> NAME/KEY: Expression cassette
<222> LOCATION: (1)..(3316)
<220> FEATURE:
<221> NAME/KEY: Ubi promoter, first exon and intron
<222> LOCATION: (1)..(1992)
<220> FEATURE:

<221> NAME/KEY: AtBAG4opt CDS
<222> LOCATION: (2016)..(2825)
<223> OTHER INFORMATION: Codon optimized AtBAG4 sequence
<220> FEATURE:
<221> NAME/KEY: 35-NOS double terminator
<222> LOCATION: (2832)..(3316)

<400> SEQUENCE: 7

| | | | | | |
|---|---|---|---|---|---|
| tgcagtgcag | cgtgacccgg | tcgtgcccct | ctctagagat | aatgagcatt | gcatgtctaa | 60 |
| gttataaaaa | attaccacat | atttttttg | tcacacttgt | ttgaagtgca | gtttatctat | 120 |
| ctttatacat | atatttaaac | tttactctac | gaataatata | atctatagta | ctacaataat | 180 |
| atcagtgttt | tagagaatca | tataaatgaa | cagttagaca | tggtctaaag | gacaattgag | 240 |
| tattttgaca | acaggactct | acagttttat | cttttttagtg | tgcatgtgtt | ctccttttt | 300 |
| tttgcaaata | gcttcaccta | taatactt | catccatttt | attagtacat | ccatttaggg | 360 |
| tttagggtta | atggttttta | tagactaatt | ttttagtac | atctatttta | ttctattta | 420 |
| gcctctaaat | taagaaaact | aaaactctat | tttagttttt | ttattaata | atttagatat | 480 |
| aaaatagaat | aaaataaagt | gactaaaaat | taaacaaata | cccttaaga | aattaaaaaa | 540 |
| actaaggaaa | cattttctt | gtttcgagta | gataatgcca | gcctgttaaa | cgccgtcgac | 600 |
| gagtctaacg | gacaccaacc | agcgaaccag | cagcgtcgcg | tcgggccaag | cgaagcagac | 660 |
| ggcacggcat | ctctgtcgct | gcctctggac | ccctctcgag | agttccgctc | caccgttgga | 720 |
| cttgctccgc | tgtcggcatc | cagaaattgc | gtggcggagc | ggcagacgtg | agccggcacg | 780 |
| gcaggcggcc | tcctcctcct | ctcacggcac | cggcagctac | ggggattcc | tttcccaccg | 840 |
| ctccttcgct | ttcccttcct | cgcccgccgt | aataaataga | cacccctcc | acaccctctt | 900 |
| tccccaacct | cgtgttgttc | ggagcgcaca | cacacacaac | cagatctccc | ccaaatccac | 960 |
| ccgtcggcac | ctccgcttca | aggtacgccg | ctcgtcctcc | ccccccccc | ctctctacct | 1020 |
| tctctagatc | ggcgttccgg | tccatggtta | gggcccggta | gttctacttc | tgttcatgtt | 1080 |
| tgtgttagat | ccgtgtttgt | gttagatccg | tgctgctagc | gttcgtacac | ggatgcgacc | 1140 |
| tgtacgtcag | acacgttctg | attgctaact | tgccagtgtt | tctctttggg | gaatcctggg | 1200 |
| atggctctag | ccgttccgca | gacgggatcg | atttcatgat | ttttttttgtt | tcgttgcata | 1260 |
| gggtttggtt | tgcccttttc | ctttattcca | atatatgccg | tgcacttgtt | tgtcgggtca | 1320 |
| tcttttcatg | cttttttttg | tcttggttgt | gatgatgtgg | tctggttggg | cggtcgttct | 1380 |
| agatcggagt | agaattctgt | ttcaaactac | ctggtggatt | tattaatttt | ggatctgtat | 1440 |
| gtgtgtgcca | tacatattca | tagttacgaa | ttgaagatga | tggatggaaa | tatcgatcta | 1500 |
| ggataggtat | acatgttgat | gcgggtttta | ctgatgcata | tacagagatg | cttttttgttc | 1560 |
| gcttggttgt | gatgatgtgg | tgtgttggg | cggtcgttca | ttcgttctag | atcggagtag | 1620 |
| aatactgttt | caaactacct | ggtgtattta | ttaattttgg | aactgtatgt | gtgtgtcata | 1680 |
| catcttcata | gttacgagtt | taagatggat | ggaaatatcg | atctaggata | ggtatacatg | 1740 |
| ttgatgtggg | ttttactgat | gcatatacat | gatggcatat | gcagcatcta | ttcatatgct | 1800 |
| ctaaccttga | gtacctatct | attataataa | acaagtatgt | tttataatta | ttttgatctt | 1860 |
| gatatacttg | gatgatggca | tatgcagcag | ctatatgtgg | attttttag | ccctgccttc | 1920 |
| atacgctatt | tatttgcttg | gtactgtttc | tttgtcgat | gctcaccctg | ttgtttggtg | 1980 |
| ttacttctgc | agtgcaggtc | gactctagag | gatccatgat | gcacaattcg | acagaggagt | 2040 |
| ccgagtggga | ggtccggcct | ggcggcatgc | tggttcagag | gagggatgat | actgcttctt | 2100 |

```
ctgaccacaa gcctcttcag gacccagatt ctgcttcggc tgctttcgct cagaccatca    2160
ggattactgt gtcgcatggc tccagccacc atgacctcca catctcagct catgccacgt    2220
tcggcgatgt taagaaggct ctggtgcaga agacaggcct cgaggcctcc gagctgaaga    2280
ttcttttccg gggcgttgag agggacgatg ctgagcagct gcaggctgct ggcgtcaagg    2340
acgctagcaa gctcgtggtc gttgtggagg ataccaacaa gagggtggag cagcagccac    2400
cagtcgttac taaggagatg gagaaggcga tcgcggctgt gaacgctgtc acgggcgagg    2460
tcgacaagct gtctgatagg gtggtcgcgc tggaggttgc tgtgaatggc ggcacacagg    2520
tcgccgttag ggagttcgac atggccgcgg agctgctcat gcggcagctt ctgaagctgg    2580
acggcatcga ggctgagggc gatgctaagg tccagcgcaa ggccgaggtt cgcaggattc    2640
agaacctcca ggaggccgtg gacaagctga aggcgaggtg cagcaatccg ttcgtggatc    2700
agtctaaggc tgccgcggtc tcaacggagt gggagtcctt cggcaacggc gtgggcagcc    2760
tcaatccccc gccacccgcc tcaccctcgg ctaatgtcac acaggactgg gagaagttcg    2820
attgagagct cgatctgtcg atcgacaagc tcgagtttct ccataataat gtgtgagtag    2880
ttcccagata agggaattag ggttcctata gggtttcgct catgtgttga gcatataaga    2940
aacccttagt atgtatttgt atttgtaaaa tacttctatc aataaaattt ctaattccta    3000
aaaccaaaat ccagtactaa aatccagatc ccccgaatta attcggcggg atctgagctg    3060
gatcgttcaa acatttggca ataaagtttc ttaagattga atcctgttgc cggtcttgcg    3120
atgattatca tataatttct gttgaattac gttaagcatg taataattaa catgtaatgc    3180
atgacgttat ttatgagatg ggttttatg attagagtcc cgcaattata catttaatac    3240
gcgatagaaa acaaaatata gcgcgcaaac taggataaat tatcgcgcgc ggtgtcatct    3300
atgttactag atcggg                                                    3316
```

<210> SEQ ID NO 8
<211> LENGTH: 4945
<212> TYPE: DNA
<213> ORGANISM: Artificial Sequence
<220> FEATURE:
<223> OTHER INFORMATION: Ubi-AtBAG4-NOST-35S-NPTII (pPTN-AtBAG4) vector
      for Agrobacterium-mediated transformation.
<220> FEATURE:
<221> NAME/KEY: Expression cassette
<222> LOCATION: (1)..(4945)
<220> FEATURE:
<221> NAME/KEY: Ubi promoter, first exon and intron
<222> LOCATION: (1)..(1992)
<220> FEATURE:
<221> NAME/KEY: AtBAG4 CDS
<222> LOCATION: (2017)..(2826)
<220> FEATURE:
<221> NAME/KEY: NOS terminator
<222> LOCATION: (2834)..(3089)
<220> FEATURE:
<221> NAME/KEY: 35S promoter
<222> LOCATION: (3546)..(4089)
<220> FEATURE:
<221> NAME/KEY: NPTII CDS
<222> LOCATION: (4164)..(4945)

<400> SEQUENCE: 8

```
tgcagtgcag cgtgacccgg tcgtgcccct ctctagagat aatgagcatt gcatgtctaa      60
gttataaaaa attaccacat attttttttg tcacacttgt ttgaagtgca gtttatctat     120
ctttatacat atatttaaac tttactctac gaataatata atctatagta ctacaataat     180
atcagtgttt tagagaatca tataaatgaa cagttagaca tggtctaaag gacaattgag     240
```

```
tatttttgaca acaggactct acagttttat cttttttagtg tgcatgtgtt ctccttttt      300 tttgcaaata gcttcaccta tataatactt catccatttt attagtacat ccatttaggg      360
tttagggtta atggttttta tagactaatt tttttagtac atctatttta ttctatttta      420
gcctctaaat taagaaaact aaaactctat tttagttttt ttatttaata atttagatat      480
aaaatagaat aaaataaagt gactaaaaat taaacaaata ccctttaaga aattaaaaaa      540
actaaggaaa cattttctt gtttcgagta gataatgcca gcctgttaaa cgccgtcgac        600
gagtctaacg gacaccaacc agcgaaccag cagcgtcgcg tcgggccaag cgaagcagac      660
ggcacggcat ctctgtcgct gcctctggac ccctctcgag agttccgctc caccgttgga      720
cttgctccgc tgtcggcatc cagaaattgc gtggcggagc ggcagacgtg agccggcacg      780
gcaggcggcc tcctcctcct ctcacggcac cggcagctac gggggattcc tttcccaccg      840
ctccttcgct ttcccttcct cgcccgccgt aataaataga caccccctcc acaccctctt      900
tccccaacct cgtgttgttc ggagcgcaca cacacacaac cagatctccc ccaaatccac      960
ccgtcggcac ctccgcttca aggtacgccg ctcgtcctcc ccccccccc ctctctacct      1020 tctctagatc ggcgttccgg tccatggtta gggcccggta gttctacttc tgttcatgtt      1080
tgtgttagat ccgtgtttgt gttagatccg tgctgctagc gttcgtacac ggatgcgacc      1140
tgtacgtcag acacgttctg attgctaact tgccagtgtt tctctttggg aatcctggg      1200 atggctctag ccgttccgca gacgggatcg atttcatgat ttttttttgtt tcgttgcata   1260 gggtttggtt tgcccttttc ctttatttca atatatgccg tgcacttgtt tgtcgggtca      1320
tcttttcatg cttttttttg tcttggttgt gatgatgtgg tctggttggg cggtcgttct      1380
agatcggagt agaattctgt ttcaaactac ctggtggatt tattaatttt ggatctgtat      1440
gtgtgtgcca tacatattca tagttacgaa ttgaagatga tggatggaaa tatcgatcta      1500
ggataggtat acatgttgat gcgggttta ctgatgcata tacagagatg cttttttgttc      1560 gcttggttgt gatgatgtgg tgtggttggg cggtcgttca ttcgttctag atcggagtag     1620
aatactgttt caaactacct ggtgtatta ttaattttgg aactgtatgt gtgtgtcata     1680
catcttcata gttacgagtt taagatggat ggaaatatcg atctaggata ggtatacatg    1740
ttgatgtggg ttttactgat gcatatacat gatggcatat gcagcatcta ttcatatgct    1800
ctaaccttga gtacctatct attataataa acaagtatgt tttataatta ttttgatctt    1860
gatatacttg gatgatggca tatgcagcag ctatatgtgg atttttttag ccctgccttc    1920
atacgctatt tatttgcttg gtactgtttc ttttgtcgat gctcaccctg ttgtttggtg    1980
ttacttctgc agtgcaggtc gactctagag gatcccatga tgcataattc aaccgaagaa    2040
tcggaatggg aggtgagacc tggtggtatg ctcgtccaac gaagagacga caccgcttcc    2100
tccgaccaca aacctctcca ggatcccgac tctgcttccg ccgcttttgc tcaaaccatc    2160
agaatcactg tttctcatgg ctcatcgcac cacgatcttc atatttctgc tcacgccact    2220
ttcggggatg taaagaaagc tcttgttcag aaaactggat tggaagctag tgaattgaag    2280
atcttgttca gaggagttga gagatgat gctgaacaat gcaagctgc tggtgttaag        2340 gatgcgtcta agcttgttgt tgttgttgag gatacgaata agagagtgga caacagcct     2400 cctgtggtaa ctaaagagat ggaaaaagct attgctgctg ttaacgcggt tacaggagag    2460
gtcgataagc tctcggatag agttgttgct ttagaagttg ctgtgaatgg agggacgcaa    2520
gttgcggtgc gggagtttga catggctgca gagcttctta tgaggcagct gctcaaattg    2580
gatggcattg aggctgaagg ggacgctaaa gtacagcgta aggctgaggt acgtagaatc    2640
```

```
caaaacttgc aggaggctgt ggataagttg aaggcaagat gttcaaatcc gtttgtggat    2700
cagagcaaag ctgcagctgt aagcactgag tgggaatcgt tcggaaacgg tgtcggaagc    2760
ttgaaccctc ctccgccagc ttcgccttcg gccaatgtaa ctcaagattg ggagaaattt    2820
gactgacgag ctcgatcgtt caaacatttg gcaataaagt ttcttaagat tgaatcctgt    2880
tgccggtctt gcgatgatta tcatataatt tctgttgaat tacgttaagc atgtaataat    2940
taacatgtaa tgcatgacgt tatttatgag atgggttttt atgattagag tcccgcaatt    3000
atacatttaa tacgcgatag aaaacaaaat atagcgcgca aactaggata aattatcgcg    3060
cgcggtgtca tctatgttac tagatcgggg aattcgtaat catggtcata gctgtttcct    3120
gtgtgaaatt gttatccgct cacaattcca cacaacatac gagccggaag cataaagtgt    3180
aaagcctggg gtgcctaatg agtgagctaa ctcacattaa ttgcgttgcg ctcactgccc    3240
gctttccagt cgggaaacct gtcgtgccag ctgcattaat gaatcggcca acgcgcgggg    3300
agaggcggtt tgcgtattgg ctagagcagc ttgccaacat ggtggagcac gacactctcg    3360
tctactccaa gaatatcaaa gatacagtct cagaagacca aagggctatt gagacttttc    3420
aacaaagggt aatatcggga aacctcctcg gattccattg cccagctatc tgtcacttca    3480
tcaaaaggac agtagaaaag gaaggtggca cctacaaatg ccatcattgc gataaaggaa    3540
aggctatcgt tcaagatgcc tctgccgaca gtggtcccaa agatggaccc ccacccacga    3600
ggagcatcgt ggaaaaagaa gacgttccaa ccacgtcttc aaagcaagtg gattgatgtg    3660
ataacatggt ggagcacgac actctcgtct actccaagaa tatcaaagat acagtctcag    3720
aagaccaaag ggctattgag acttttcaac aaagggtaat atcgggaaac ctcctcggat    3780
tccattgccc agctatctgt cacttcatca aaaggacagt agaaaaggaa ggtggcacct    3840
acaaatgcca tcattgcgat aaaggaaagg ctatcgttca agatgcctct gccgacagtg    3900
gtcccaaaga tggaccccca cccacgagga gcatcgtgga aaaagaagac gttccaacca    3960
cgtcttcaaa gcaagtggat tgatgtgata tctccactga cgtaagggat gacgcacaat    4020
cccactatcc ttcgcaagac ccttcctcta tataaggaag ttcatttcat ttggagagga    4080
cacgctgaaa tcaccagtct ctctctacaa atctatctct ctcgattcgc agatctgtcg    4140
atcgaccatg gggattgaac aagatggatt gcacgcaggt tctccggccg cttgggtgga    4200
gaggctattc ggctatgact gggcacaaca gacaatcggc tgctctgatg ccgccgtgtt    4260
ccggctgtca gcgcaggggc gcccggttct ttttgtcaag accgacctgt ccggtgccct    4320
gaatgaactc caggacgagg cagcgcggct atcgtggctg gccacgacgg gcgttccttg    4380
cgcagctgtg ctcgacgttg tcactgaagc gggaagggac tggctgctat tgggcgaagt    4440
gccggggcag gatctcctgt catctcacct tgctcctgcc gagaaagtat ccatcatggc    4500
tgatgcaatg cggcggctgc atacgcttga tccggctacc tgcccattcg accaccaagc    4560
gaaacatcgc atcgagcgag cacgtactcg gatggaagcc ggtcttgtcg atcaggatga    4620
tctggacgaa gagcatcagg ggctcgcgcc agccgaactg ttcgccaggc tcaaggcgcg    4680
catgcccgac ggcgaggatc tcgtcgtgac acatggcgat gcctgcttgc cgaatatcat    4740
ggtggaaaat ggccgctttt ctggattcat cgactgtggc cggctgggtg tggcggaccg    4800
ctatcaggac atagcgttgg ctacccgtga tattgctgaa gagcttggcg gcgaatgggc    4860
tgaccgcttc ctcgtgcttt acggtatcgc cgctcccgat tcgcagcgca tcgccttcta    4920
tcgccttctt gacgagttct tctga                                          4945
```

<210> SEQ ID NO 9
<211> LENGTH: 720
<212> TYPE: DNA
<213> ORGANISM: Homo sapiens

<400> SEQUENCE: 9

```
atggcgcacg ctgggagaac ggggtacgat aaccgggaga tagtgatgaa gtacatccat      60
tataagctgt cgcagagggg ctacgagtgg gatgcgggag atgtgggcgc cgcgcccccg     120
ggggccgccc ccgcaccggg catcttctcc tcccagcccg gcacacgcc ccatccagcc      180
gcatcccggg accggtcgc caggacctcg ccgctgcaga ccccggctgc ccccggcgcc     240
gccgcgggc ctgcgctcag cccggtgcca cctgtggtcc acctgaccct ccgccaggcc     300
ggcgacgact ctcccgccg ctaccgccgc gacttcgccg agatgtccag ccagctgcac     360
ctgacgccct tcaccgcgcg gggacgcttt gccacggtgg tggaggagct cttcagggac    420
gggggtgaact gggggaggat tgtggccttc tttgagttcg gtggggtcat gtgtgtggag    480
agcgtcaacc gggagatgtc gccccctggtg gacaacatcg ccctgtggat gactgagtac   540
ctgaaccggc acctgcacac ctggatccag ataacggag gctgggatgc ctttgtggaa    600
ctgtacggcc ccagcatgcg gcctctgttt gatttctcct ggctgtctct gaagactctg    660
ctcagtttgg ccctggtggg agcttgcatc accctgggtg cctatctggg ccacaagtga   720
```

<210> SEQ ID NO 10
<211> LENGTH: 239
<212> TYPE: PRT
<213> ORGANISM: Homo sapiens

<400> SEQUENCE: 10

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

-continued

```
Leu Phe Asp Phe Ser Trp Leu Ser Leu Lys Thr Leu Leu Ser Leu Ala
    210                 215                 220
Leu Val Gly Ala Cys Ile Thr Leu Gly Ala Tyr Leu Gly His Lys
225                 230                 235
```

COMPOSITIONS, ORGANISMS, SYSTEMS, AND METHODS FOR ALTERING COLD, DROUGHT, AND SALT TOLERANCE IN PLANTS

CROSS-REFERENCE TO RELATED APPLICATIONS

This application claims priority to U.S. Provisional Application No. 61/852,242 filed Mar. 15, 2013, the contents of which are hereby incorporated in their entirety by reference.

FIELD OF THE DISCLOSURE

The present disclosure relates, in some embodiments, to materials, systems, organisms, and methods for altering (e.g., improving) abiotic stress tolerance in plants and/or plant biomass.

BACKGROUND OF THE DISCLOSURE

To the extent they exist at all, materials, systems, organisms, and methods for enhancing abiotic stress tolerance in sugarcane are inefficient, inoperable, and/or attended by undesirable properties.

SUMMARY

Accordingly, a need has arisen for improved materials, systems, organisms, and methods for enhancing abiotic stress tolerance in plants (e.g., sugarcane).

The present disclosure relates, according to some embodiments, to materials, systems, organisms, and methods for enhancing abiotic stress tolerance in plants (e.g., sugarcane) and/or plant biomass. For example, a plant (e.g., a sugarcane plant) having improved abiotic stress tolerance and/or plant biomass over a corresponding wild-type plant may comprise an expression control sequence operable in the host (e.g., constitutive, tissue-specific, inducible), and/or an expressible nucleic acid sequence encoding an amino acid sequence of an *Arabidopsis thaliana* BCL-2-associated athanogene 4 (AtBAG4) sequence, a *Caenorhabditis elegans* Ced-9 sequence, and/or a human Bcl-2-161 sequence operably linked to the expression control sequence. Encoded amino acid sequences may be SEQ ID NO: 2, SEQ ID NO: 4, SEQ ID NO: 10 and/or sequences having, for example, 85% identity thereto. Expressible nucleic acid sequences may be SEQ ID NO: 1, SEQ ID NO: 3, nucleotides 2135-2980 of SEQ ID NO: 5, nucleotides 2017-2826 of SEQ ID NO: 6, nucleotides 2016-2825 of SEQ ID NO: 7, nucleotides 2017-2826 of SEQ ID NO: 8, and SEQ ID NO: 9, and/or sequences having, for example, 85% identity thereto. Improved abiotic stress tolerance may include improved cold tolerance, improved drought tolerance, improved heat tolerance, improved wind resistance, and/or combinations thereof, according to some embodiments. Plants comprising an expressible nucleic acid may have substantially the same performance (e.g., growth performance, agronomic performance) as corresponding wild-type plants when both are grown under the same greenhouse conditions. For example, plants comprising an expressible nucleic acid may have substantially the same stem height, leaf area, dry mass, sugar content, and/or days to flowering as the corresponding wild-type plant. Plants comprising an expressible nucleic acid may perform differently, in some embodiments. For example, plants comprising a Ced-9 sequence may have more tillers and/or a higher plant dry mass under normal growth conditions. In some embodiments, an expression control sequence may comprise a promoter (e.g., a ubiquitin promoter, a CaMV35S promoter).

The present disclosure relates, in some embodiments, to methods of producing plants (e.g., sugarcane) having improved abiotic stress tolerance over corresponding wild-type plants. For example, a method may comprise contacting a plant cell (e.g., a sugarcane plant cell) with a nucleic acid under conditions that permit incorporation of at least a portion of the nucleic acid into the host genome (e.g., chromosomal, mitochondrial, or plastid genome) and/or regenerating a plant from the contacted plant cell. Contacting may include, for example, any desired plant transformation method. An incorporated nucleic acid may comprise an expression control sequence operable in the host, and/or an expressible nucleic acid sequence encoding an amino acid sequence of an *Arabidopsis thaliana* BCL-2-associated athanogene 4 (AtBAG4) sequence, a *Caenorhabditis elegans* Ced-9 sequence, and/or a human Bcl-2-161 sequence. Encoded amino acid sequences may be SEQ ID NO: 2, SEQ ID NO: 4, SEQ ID NO: 10, and/or sequences having, for example, 85% identity thereto. Expressible nucleic acid sequences may be SEQ ID NO: 1, SEQ ID NO: 3, nucleotides 2135-2980 of SEQ ID NO: 5, nucleotides 2017-2826 of SEQ ID NO: 6, nucleotides 2016-2825 of SEQ ID NO: 7, nucleotides 2017-2826 of SEQ ID NO: 8, and SEQ ID NO: 9, and/or sequences having, for example, 85% identity thereto. Improved abiotic stress tolerance may include improved cold tolerance, improved drought tolerance, improved heat tolerance, improved wind resistance, and/or combinations thereof, according to some embodiments. Plants comprising an expressible nucleic acid may have substantially the same performance (e.g., growth performance, agronomic performance) as corresponding wild-type plants when both are grown under the same greenhouse conditions. For example, plants comprising an expressible nucleic acid may have substantially the same stem height, leaf area, dry mass, sugar content, and/or days to flowering as the corresponding wild-type plant. Plants comprising an expressible nucleic acid may perform differently, in some embodiments. For example, plants comprising a Ced-9 sequence may have more tillers and/or a higher plant dry mass under normal growth conditions. In some embodiments, an expression control sequence may comprise a promoter (e.g., a ubiquitin promoter, a CaMV35S promoter).

In some embodiments, the present disclosure relates to expression cassettes and/or expression vectors for improving abiotic stress tolerance and/or increasing biomass in a plant (e.g., a sugarcane plant). For example, an expression cassette and/or expression vector may comprise, in a 5' to 3' direction (a) an expression control sequence operable in the sugarcane host plant, (b) a nucleic acid sequence that encodes a desired amino acid sequence (e.g., AtBAG4, Ced-9) or nucleic acids (e.g., Bcl2-161), and/or (c) a terminator operable in the host plant. In some embodiments, a desired amino acid sequence may be selected from SEQ ID NOS: 2, SEQ ID NO: 4, SEQ ID NO: 10, and/or sequences having, for example, 85% identity thereto. A nucleic acid sequence that encodes a desired amino acid sequence, according to some embodiments, may be selected from SEQ ID NO: 1, SEQ ID NO: 3, nucleotides 2135-2980 of SEQ ID NO: 5, nucleotides 2017-2826 of SEQ ID NO: 6, nucleotides 2016-2825 of SEQ ID NO: 7, nucleotides 2017-2826 of SEQ ID NO: 8, and SEQ ID NO: 9, and/or sequences having, for example, 85% identity thereto. In some embodiments, an expression control sequence may comprise a promoter (e.g., a ubiquitin promoter, a CaMV35S promoter). A terminator, in some embodiments, may be selected from any desired terminator operable in a selected host plant. Examples of terminators include a 35S terminator and/or a NOS terminator.

The present disclosure relates, in some embodiments, to microorganisms for improving abiotic stress tolerance and/or increasing biomass in a plant (e.g., a sugarcane plant). For example, a microorganism (e.g., *Agrobacterium, E. coli*) may comprise an expression cassette and/or expression vector comprising, in a 5' to 3' direction (a) an expression control sequence operable in the sugarcane host plant, (b) a nucleic acid sequence that encodes a desired amino acid sequence (e.g., AtBAG4, Ced-9) or nucleic acids (e.g., Bgl2-161), and/or (c) a terminator operable in in the host plant. In some embodiments, a desired amino acid sequence may be selected from SEQ ID NOS: 2, SEQ ID NO: 4, SEQ ID NO: 10, and/or sequences having, for example, 85% identity thereto. A nucleic acid sequence that encodes a desired amino acid sequence, according to some embodiments, may be selected from SEQ ID NO: 1, SEQ ID NO: 3, nucleotides 2135-2980 of SEQ ID NO: 5, nucleotides 2017-2826 of SEQ ID NO: 6, nucleotides 2016-2825 of SEQ ID NO: 7, nucleotides 2017-2826 of SEQ ID NO: 8, and SEQ ID NO: 9, and/or sequences having, for example, 85% identity thereto. In some embodiments, an expression control sequence may comprise a promoter (e.g., a ubiquitin promoter, a CaMV35S promoter). A terminator, in some embodiments, may be selected from any desired terminator operable in a selected host plant. Examples of terminators include a 35S terminator and/or a NOS terminator.

According to some embodiments, the present disclosure relates to isolated and/or purified nucleic acids encoding a desired amino acid sequence (e.g., AtBAG4, Ced-9, Bcl-2-161) and comprising a nucleic acid sequence selected from the group consisting of SEQ ID NO: 1, SEQ ID NO: 3, nucleotides 2135-2980 of SEQ ID NO: 5, nucleotides 2017-2826 of SEQ ID NO: 6, nucleotides 2016-2825 of SEQ ID NO: 7, nucleotides 2017-2826 of SEQ ID NO: 8, and SEQ ID NO: 9, wherein the encoded protein is operable to enhance abiotic stress performance and/or plant biomass.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein:

FIG. 11A illustrates salinity stress of control plants according to a specific example embodiment of the disclosure FIG. 11B illustrates salinity stress Bcl2-161 plants according to a specific example embodiment of the disclosure FIG. 11C illustrates salinity stress of control and Bcl2-161 plants according to a specific example embodiment of the disclosure;

FIG. 12 illustrates salt stress of AtBAG4 plants according to a specific example embodiment of the disclosure;

FIG. 13A illustrates wild type sugarcane plants afflicted with irreversible cold damage according to a specific example embodiment of the disclosure;

FIG. 13B illustrates cold tolerance of Ced-9 transgenic plants according to a specific example embodiment of the disclosure;

BRIEF DESCRIPTION OF THE SEQUENCE LISTING

Figure 1A:
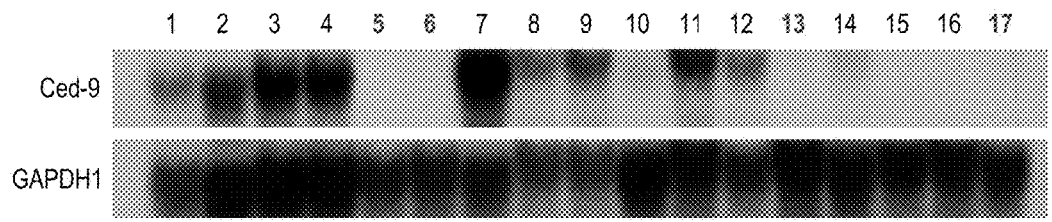
FIG. 1A illustrates a northern blot of sugarcane according to a specific example embodiment of the disclosure.

Some embodiments of the disclosure may be understood by referring, in part, to the present disclosure and the accompanying sequence listing, wherein:

SEQ ID NO: 1 illustrates an AtBAG4 (NM_115037) nucleic acid sequence according to specific example embodiments of the disclosure;

SEQ ID NO: 2 illustrates an AtBAG4 (NM_115037) amino acid sequence according to specific example embodiments of the disclosure;

SEQ ID NO: 3 illustrates a Ced-9 (NC_003281) nucleic acid sequence according to specific example embodiments of the disclosure;

SEQ ID NO: 4 illustrates a Ced-9 (NC_003281) amino acid sequence according to specific example embodiments of the disclosure;

SEQ ID NO: 5 illustrates a Ubi-Ced9-35ST (pTEM09) vector nucleic acid sequence for biolistic bombardment according to specific example embodiments of the disclosure;

SEQ ID NO: 6 illustrates a Ubi-AtBAG4-NOST (pTEM10) vector nucleic acid sequence for biolistic bombardment according to specific example embodiments of the disclosure;

SEQ ID NO: 7 illustrates a Ubi-AtBAG4opt-35S-NOST (pTEM113) vector nucleic acid sequence for biolistic bombardment according to specific example embodiments of the disclosure;

SEQ ID NO: 8 illustrates a Ubi-AtBAG4-NOST-35S-NPTII (pPTN-AtBAG4) vector nucleic acid sequence for *Agrobacterium*-mediated transformation according to specific example embodiments of the disclosure;

SEQ ID NO: 9 illustrates a Bcl-2 nucleic acid sequence according to specific example embodiments of the disclosure; and SEQ ID NO: 10 illustrates a Bcl-2 (AAH27258.1) amino acid sequence according to specific example embodiments of the disclosure.

DETAILED DESCRIPTION

The present disclosure relates, in some embodiments, to materials, systems, organisms, and methods for altering (e.g., enhancing) abiotic stress tolerance (e.g., cold, salinity, drought, heat, wind) and/or enhancing biomass in plants. For example, enhancing abiotic stress tolerance may be achieved using nucleic acids and/or polypeptides of an *Arabidopsis thaliana* BCL-2-associated athanogene 4 (AtBAG4), a *Caenorhabditis elegans* Ced-9, and/or a human BCl-2-161. In some embodiments, a nucleic acid may be codon optimized for expression in a plant (e.g., sugarcane).

I. Compositions

A. Nucleic Acids

The present disclosure relates, in some embodiments, nucleic acids operable in sugarcane to enhance abiotic stress tolerance. According to some embodiments, a nucleic acid may comprise a nucleic acid sequence having at least about 85% identity to one or more sequences selected from SEQ ID NOS: 1, 3, 5-9, and fragments thereof, at least about 90% identity to one or more sequences selected from SEQ ID NOS: 1, 3, 5-9, and fragments thereof, at least about 95% identity to one or more sequences selected from SEQ ID NOS: 1, 3, 5-9, and fragments thereof, at least about 98% identity to one or more sequences selected from SEQ ID NOS: 1, 3, 5-9, and fragments thereof, at least about 99% identity to one or more sequences selected from SEQ ID NOS: 1, 3, 5-9, and fragments thereof, and/or at least about 100% identity to one or more sequences selected from SEQ ID NOS: 1, 3, 5-9, and fragments thereof. Fragments may include sequences corresponding to an expression control sequence, a 5' UTR, a coding sequence, a 3' UTR, and/or a terminator.

The present disclosure relates, according to some embodiments, to one or more nucleic acid sequences like SEQ ID NOS: 1, 3, 5-9, and fragments thereof expressible in at least one monocot and/or at least one dicot. For example, a nucleic acid sequence may include a nucleic acid sequence that differs from SEQ ID NOS: 1, 3, 5-9, and fragments thereof at one or more positions. A nucleic acid sequence, according to some embodiments, may hybridize to a nucleic acid having the nucleotide sequence set forth in the appended Sequence Listing under stringent conditions. Stringent conditions may include, for example, (a) 4×SSC at 65° C. followed by 0.1×SSC at 65° for 60 minutes and/or (b) 50% formamide, 4×SSC at 65° C. A nucleic acid sequence may comprise a fragment (e.g., a deletion fragment) of a nucleic acid having a sequence set forth in the appended Sequence Listing and be operable to enhance abiotic stress tolerance (e.g., cold, salinity, drought, heat, wind). One of ordinary skill in the art having the benefit of the present disclosure may prepare one or more fragments (e.g., a deletion fragments) of a nucleic acid having a sequence set forth in the appended Sequence Listing. Functionality of a nucleic acid and/or amino acid sequence like, but not identical to, one of the sequences disclosed herein may be assessed, in some embodiments, by one or more desired metrics. For example catalytic activity and binding affinity of enzymes and transcription factors may be assessed. In some embodiments, a sequence may be deemed to be functional where it performs substantially the same as the sequence to which it is compared and/or substantially the same as the wild-type.

A nucleic acid sequence having a sequence like SEQ ID NOS: 1, 3, 5-9, and fragments thereof may be identified by database searches using the promoter or elements thereof as the query sequence using the Basic Local Alignment Search Tool (BLAST®) algorithm (Altschul et al., 1997 Nucl. Acids Res. 25:3389-3402) with the BLOSUM62 Matrix, a gap cost of 11 and persistence cost of 1 per residue and an E value of 10. Sequence identity may be assessed by any available method according to some embodiments. For example, two sequences may be compared with either ALIGN (Global alignment) or LALIGN (Local homology alignment) in the FASTA suite of applications (Pearson and Lipman, 1988 Proc. Nat. Acad. Sci. 85:2444-24448; Pearson, 1990 Methods in Enzymology 183:63-98) with the BLOSUM50 matrix and gap penalties of −16, −4. Sequence similarity may be assessed according to ClustalW (Larkin et al., 2007, Bioinformatics 23(21): 2947-2948), Basic Local Alignment Search Tool (BLAST®), FASTA, or similar algorithm. A consensus sequence may be deduced from two or more sequences using common multiple sequence alignment programs such as ClustalW, Muscle, MAFFT and T-Coffee (Nuin et al., 2006, BMC Bioinformatics 7:471 (1-18).

According to some embodiments, a nucleic acid sequence may be modified at one or more positions pursuant to available codon optimization protocols. For example, a coding sequence may be codon optimized for expression in a desired host (e.g., sugarcane). In some embodiments, a nucleic acid may be used in its sense orientation and/or its antisense orientation.

B. Polypeptides

The present disclosure relates, in some embodiments, polypeptides operable in sugarcane to enhance stress tolerance and/or biomass yield. According to some embodiments, a polypeptide may comprise an amino acid sequence having at least about 85% identity to one or more sequences selected from SEQ ID NOS: 2, 4, and 10, at least about 90% identity to one or more sequences selected from SEQ ID NOS: 2, 4, and 10, at least about 95% identity to one or more sequences selected from SEQ ID NOS: 2, 4, and 10, at least about 98% identity to one or more sequences selected from SEQ ID NOS: 2, 4, and 10, at least about 99% identity to one or more sequences selected from SEQ ID NOS: 2, 4, and 10, and/or at least about 100% identity to one or more sequences selected from SEQ ID NOS: 2, 4, and 10.

C. Expression Cassettes and Vectors

The disclosure relates, in some embodiments, to expression vectors and/or expression cassettes for expressing a nucleic acid sequence (e.g., a coding sequence, an inverted repeat, and an artificial microRNA (amiRNA)) in a cell and comprising an expression control sequence and the nucleic acid sequence operably linked to the expression control sequence. Thus, for example, an expression cassette may comprise a heterologous coding sequence, the expression of which may be desired in a plant (e.g., sugarcane). In some embodiments, an expression vector may be selected from the vector shown in FIGS. 18-23.

The disclosure relates, in some embodiments, to an expression vector, which may comprise, for example, a nucleic acid having an expression control sequence and a coding sequence operably linked to the expression control sequence. In some embodiments, an expression control sequence may comprise one or more promoters, one or more operators, one or more enhancers, one or more ribosome binding sites, and/or combinations thereof. An expression control sequence may comprise, for example, a nucleic acid having promoter activity. An expression control sequence, according to some embodiments, may be constitutively active or conditionally active in (a) an organ selected from root, leaf, stem, flower, seed, and/or fruit, and/or (b) active in a tissue selected from epidermis, periderm, parenchyma, collenchyma, sclerenchyma, xylem, phloem, and/or secretory structures. An expression control sequence, according to some embodiments, may be operable to drive expression of a nucleic acid sequence (e.g., a coding sequence) in a cell. Metrics for expression may include, for example, rate of appearance and/or accumulation of a gene product (e.g., RNA and/or protein) and/or total accumulation of a gene product as of one or more time points (e.g., elapsed time after a starting point and/or a stage of development). Comparative assays for gene products may be qualitative, semi-quantitative, and/or quantitative in some embodiments. Comparative assays may indirectly and/or directly assess the presence and/or amount of gene product. In some embodiments, an expression control sequence may be sensitive to one or more stimuli (e.g., one or more small molecules, one or more plant defense-inducing agents, mechanical damage, temperature, pressure). For example, activity of an expression control sequence may be enhanced or suppressed upon infection with a microorganism (e.g., a bacterium or a virus).

An expression vector, in some embodiments, may be contacted with a cell (e.g., a plant cell) under conditions that permit expression (e.g., transcription) of the coding sequence. An expression vector may be contacted with a plant cell (e.g., an embryonic cell, a stem cell, a callous cell) under conditions that permit expression of the coding sequence in the cell and/or cells derived from the plant cell according to some embodiments. An expression vector may be contacted with a cell (e.g., a plant cell), in some embodiments, under conditions that permit inheritance of at least a portion of the expression vector in the cell's progeny. According to some embodiments, an expression vector may include one or more selectable markers. For example, an expression vector may include a marker for selection when the vector is in a bacterial host, a yeast host, and/or a plant host.

II. Microorganisms

The present disclosure relates, in some embodiments, to a microorganism comprising a peptide (e.g., a heterologous peptide of any desired size) and/or a nucleic acid (e.g., a heterologous and/or expressible nucleic acid) comprising a nucleic acid sequence encoding a peptide. For example, a microorganism may comprise a bacterium, a yeast, and/or a virus. Examples of microorganisms may include, without limitation, *Agrobacterium tumefaciens*, *Escherichia coli*, a lepidopteran cell line, a Rice tungro baciliiform virus, a *Commelina* yellow mosaic virus, a Banana streak virus, a Taro baciliiform virus, and/or baculovirus. According to some embodiments, a peptide may be tolerated by and/or innocuous to its host microorganism. A microorganism may comprise an expression control sequence and a peptide coding sequence operably linked to the expression control sequence. A nucleic acid (e.g., a heterologous and/or expressible nucleic acid) comprising a nucleic acid sequence encoding a peptide may be present, in some embodiments, on a genomic nucleic acid and/or an extra-genomic nucleic acid. A peptide may be selected from an *Arabidopsis thaliana* BCL-2-associated athanogene 4 (AtBAG4), a *Caenorhabditis elegans* Ced-9, and/or a human Bcl-2-161. A nucleic acid may comprise a codon-optimized sequence for expressing AtBAG4, Ced-9, and/or Bcl-2-161 protein in a plant.

III. Plants

The present disclosure relates, in some embodiments, to a plant cell (e.g., an embryonic cell, a stem cell, a callous cell), a tissue, and/or a plant comprising a peptide (e.g., a heterologous peptide) and/or a nucleic acid (e.g., a heterologous and/or expressible nucleic acid) comprising a nucleic acid sequence encoding a peptide. A plant and/or plant cell may be selected from a monocot and/or a dicot in some embodiments. Examples of a monocot may include, without limitation, sugarcane, miscanthus, a miscanthus x sugarcane hybrid, switch grass, oats, wheat, barley, maize, rice, banana, yucca, onion, asparagus, and/or sorghum. Examples of a dicot may include, without limitation, coffee, tomato, pepper, tobacco, lima bean, *Arabidopsis*, rubber, orange, grapefruit, potato, squash, pea, forest trees (e.g., poplar and eucalyptus), and/or sugar beet. A plant cell may be included in a plant tissue, a plant organ, and/or a whole plant in some embodiments. A plant cell in a tissue, organ, and/or whole plant may be adjacent, according to some embodiments, to one or more isogenic cells and/or one or more heterogenic cells. In some embodiments, a plant may include primary transformants and/or progeny thereof. A plant comprising a nucleic acid (e.g., a heterologous and/or expressible nucleic acid) comprising a nucleic acid sequence encoding a peptide may further comprise an expression control sequence operably linked to the nucleic acid, in some embodiments. A nucleic acid sequence encoding a peptide may be expressed, according to some embodiments, in a plant in one or more up to all (e.g., substantially all) organs, tissues, and/or cell types including, without limitation, stalks, leaves, roots, seeds, flowers, fruit, meristem, parenchyma, storage parenchyma, collenchyma, sclerenchyma, epidermis, mesophyll, bundle sheath, guard cells, protoxylem, metaxylem, phloem, phloem companion, and/or combinations thereof. In some embodiments, a nucleic acid and/or its gene product (e.g., a peptide) may be located in and/or translocated to one or more organelles (e.g., vacuoles, chloroplasts, mitochondria, plastids).

IV. Methods

A. Transforming a Plant

The present disclosure relates, according to some embodiments, to methods for independent transformation of a plant (e.g., sugarcane). For example, a method may comprise independent transformation, using *Agrobacterium tumefaciens* (At), of the native sugarcane genome. Transforming may comprise, in some embodiments, biolistically bombarding a plant and/or a plant cell with a particle comprising an expression cassette and/or co-cultivating a plant with an *Agrobacterium* cell comprising the expression cassette. A method may comprise, in some embodiments, regenerating a plant from a transformed cell (e.g., embryogenic callus) to form one or more progeny of the transformed cell. A method may comprise cultivating and/or breeding progeny of a transformed cell in some embodiments.

A transformation method may comprise contacting a nucleic acid comprising a nucleic acid sequence having at least 85% identity with a nucleic acid sequence selected from SEQ ID NOS: 1, 3, functional fragments thereof (e.g., fragments annotated as corresponding to a coding sequence), and/or combinations thereof with a sugarcane plant according to some embodiments. A transformed plant (e.g., a transformed genome of a sugarcane cultivar) may independently contain, in some embodiments, a nucleic acid comprising a nucleic acid sequence selected from an *Arabidopsis thaliana* BCL-2-associated athanogene 4 (AtBAG4) sequence, a codon-optimized *Arabidopsis thaliana* BCL-2-associated athanogene 4 (AtBAG4) sequence, a *Caenorhabditis elegans* Ced-9 sequence, a codon-optimized *Caenorhabditis elegans* Ced-9 sequence, a human Bcl2-2161, and/or a codon-optimized human Bcl-2-161. According to some embodiments, a transformed sugarcane plant may comprise a peptide encoded by an *Arabidopsis thaliana* BCL-2-associated athanogene 4 (AtBAG4) sequence, a *Caenorhabditis elegans* Ced-9 sequence, and/or a human Bcl-2-161 sequence.

A transformed plant may display substantially the same performance (e.g., growth performance, agronomic performance) as corresponding wild-type plants when both are grown under the same greenhouse conditions. Greenhouse conditions may comprise, for example, about 12-hour days at about 80° F. and about 80% relative humidity with at least once daily watering. For example, plants comprising an expressible nucleic acid may have substantially the same stem height, leaf area, dry mass, sugar content, and/or days to flowering as the corresponding wild-type plant. Substantially the same performance may comprise, for example, a representative sample of transformed plants differing from a representative sample of wild type plants by no more than about 10%, no more than about 5%, or no more than about 2% with respect to stem height, leaf area, dry mass, sugar content, and/or days to flowering.

A transformed plant may display enhanced abiotic stress tolerance (e.g., cold, salinity, drought, heat, wind) and/or biomass yield compared to the corresponding wild-type plant grown under the same conditions. As will be understood by those skilled in the art who have the benefit of the instant disclosure, other equivalent or alternative compositions, devices, methods, and systems for altering (e.g., enhancing) abiotic stress tolerance (e.g., cold, salinity, drought, heat, wind) and biomass can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of expression control sequences, coding sequences, linkers, and/or terminator sequences may be varied. Each disclosed method and method step may be performed in association with any other disclosed method or method step and in any order according to some embodiments. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. For example, a composition, device, and/or system may be prepared and or used as appropriate for microbes and/or plants (e.g., with regard to sanitary, infectivity, safety, toxicity, biometric, and other considerations).

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/− about 10%, depicted value +/− about 50%, depicted value +/− about 100%) and/or a range endpoint. With respect to the former, a value of 50 depicted in an example, table, and/or drawing may form the basis of a range of, for example, about 45 to about 55, about 25 to about 100, and/or about 0 to about 100.

These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

EXAMPLES

Some specific example embodiments of the disclosure may be illustrated by one or more of the examples provided herein.

Example 1

Identification of BAG Genes in Plants

The trait genes Ced-9 (Cell death abnormal) from *Caenorhabditis elegans*, AtBAG4 (*A. thaliana* Bcl-2-associated athanogene), and Bcl-2-161 from humans, belong to the BAG (BCl-2 associated athanogene) gene family. BAG homologs from diverse kingdoms and genera may have low sequence identities and similarities (Elena V. Doukhanina et al., The Journal of Biological Chemistry, Vol. 281, No. 27, 18793-18801). For example, the conserved BAG domain (BD) of the *Arabidopsis* BAG gene family shares only (13-25%) identity with animal BAG proteins. Therefore, identifying BAG homologs may benefit from search methods such as hidden Markov model (HMM) protein searches and profile-profile alignment algorithms.

The conserved C-terminal BD domain comprises 3α helices (Elena V. Doukhanina et al., The Journal of Biological Chemistry, Vol. 281, No. 27, 18793-18801). In humans, the second and third a helices directly interact with the ATPase domain of heat-shock protein 70 (Hsp70)/heat-shock cognate 70 (Hsc70) chaperones. By modulating chaperone activity, human BAG genes control programmed cell death. Protein modelling reveals that AtBAG4 is structurally similar to human BAG4 protein and retains the 3α helices. Furthermore, pull-down assays reveal that AtBAG4 successfully binds to *Arabidopsis* Hsc70 and has similar Hsc-70 binding surfaces to the human homolog.

The Ced-9 (Cell death abnormal) from *Caenorhabditis elegans* is also a BAG homolog and is predicted to have similar protein structure and chaperone binding capabilities in *C. elegans* to the human BAG4.

Example 2

Figure 1B:
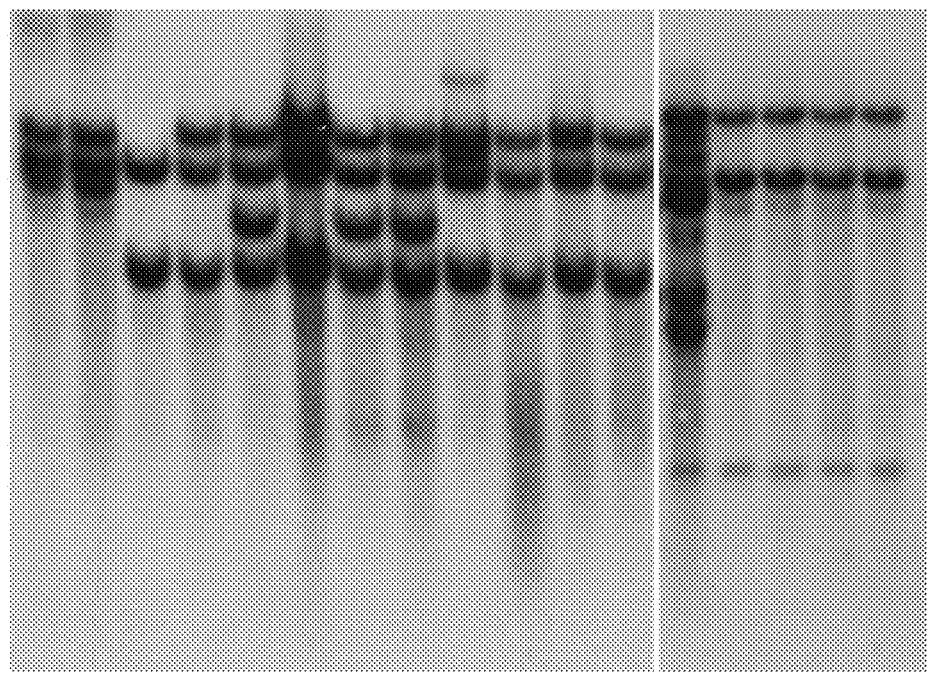
FIG. 1B illustrates a Southern blot according to a specific example embodiment of the disclosure.

Characterization of Biolistically Transformed Plants: AtBAG4, Ced-9 and Codon Optimized AtBAG4+Ced-9 Co-transformed Lines Biolistically transformed plants representing a total of 38 transformation events have been developed and characterized for the co-introduced selectable marker gene (bar) and the trait genes Ced-9 (Cell death abnormal) from *Caenorhabditis elegans* or AtBAG4 (*A. thaliana* Bcl-2-associated athanogene). Copy number of insertions and expression level of the transcripts have been determined using Southern and northern blots, respectively, for both trait genes. The determined copy number for trait genes varied from as few as 2 to over 15 copies. Each of these different events displays distinct expression levels of the trait genes and there is no evident relationship between copy number and transgene expression. While each event tends to have a distinct expression level, there are also variations in the expression levels within each event (e.g., FIG. 1A). FIG. 1 illustrates an example of transgene integration and expression patterns in sugarcane. FIG. 1A is a northern blot showing expression of the trait gene Ced-9 (six-hour exposure). Lanes in red are non-transgenic controls. Lanes 15 and 16 showed detectable transgene expression after 3 days of exposure. GAPDH1 is sugarcane glyceraldehyde 3-phosphate dehydrogenase-1, a housekeeping gene used as an internal control for equal loading of the RNA. The samples used in the northern blot do not reflect individual transformation events, rather the samples comprise mixtures RNA. Mixed samples were used to evaluate the variability of transgene expression. FIG. 1B is a Southern blot showing transgene copy number for AtBAG4. Transformation with the codon optimized AtBAG4 gene has yielded a total of 29 transgenic sugarcane plants (Table 1).

Table 1 illustrates the results of northern and Southern blot analysis of multiple biolistic transformation experiments to identify the specific transformation even present in each transformed plant. BAR dipsticks were used to pre-screen the plants recovered from tissue culture. Approximately 95% of plants growing in the selective medium tested positive for a selectable marker using the BAR screen. Those columns labeled NA consist of transgenic plants that tested positive using the BAR screen.

TABLE 1

Transformation experiments, transgenes, and sugarcane varieties.

| Transformation Experiment | Plant | Variety | Construct | Transgene | Southern Blot Results Event | Northern Blot Results Event |
|---|---|---|---|---|---|---|
| S-135 | 15 | TCP97-3388 | pTEM10 | AtBAG4 | 1 | 1 |
| S-135 | 24 | TCP97-3388 | pTEM10 | AtBAG4 | 6 | 6 |
| S-135 | 2 | TCP97-3388 | pTEM10 | AtBAG4 | 1 | 1 |
| S-135 | 12 | TCP97-3388 | pTEM10 | AtBAG4 | 2 | 2 |
| S-135 | 4 | TCP97-3388 | pTEM10 | AtBAG4 | 2 | 2 |

TABLE 1-continued

Transformation experiments, transgenes, and sugarcane varieties.

| Transformation Experiment | Plant | Variety | Construct | Transgene | Southern Blot Results Event | Northern Blot Results Event |
|---|---|---|---|---|---|---|
| S-135 | 3 | TCP97-3388 | pTEM10 | AtBAG4 | 1 | 1 |
| S-135 | 1 | TCP97-3388 | pTEM10 | AtBAG4 | 1 | 1 |
| S-135 | 6 | TCP97-3388 | pTEM10 | AtBAG4 | 2 | 2 |
| S-135 | 18 | TCP97-3388 | pTEM10 | AtBAG4 | 1 | 1 |
| S-135 | 17 | TCP97-3388 | pTEM10 | AtBAG4 | 2 | 2 |
| S-135 | 11 | TCP97-3388 | pTEM10 | AtBAG4 | NA | NA |
| S-135 | 5 | TCP97-3388 | pTEM10 | AtBAG4 | 2 | 2 |
| S-135 | 8 | TCP97-3388 | pTEM10 | AtBAG4 | 3 | 3 |
| S-135 | 23 | TCP97-3388 | pTEM10 | AtBAG4 | 1 | 1 |
| S-135 | 25 | TCP97-3388 | pTEM10 | AtBAG4 | 1 | 1 |
| S-135 | 16 | TCP97-3388 | pTEM10 | AtBAG4 | 1 | 1 |
| S-135 | 26 | TCP97-3388 | pTEM10 | AtBAG4 | 2 | 2 |
| S-135 | 14 | TCP97-3388 | pTEM10 | AtBAG4 | 1 | 1 |
| S-135 | 7 | TCP97-3388 | pTEM10 | AtBAG4 | 1 | 1 |
| S-135 | 8 | TCP97-3388 | pTEM10 | AtBAG4 | 3 | 3 |
| S-135 | 13 | TCP97-3388 | pTEM10 | AtBAG4 | 5 | 5 |
| S-135 | 10 | TCP97-3388 | pTEM10 | AtBAG4 | 1 | 1 |
| S-135 | 11 | TCP97-3388 | pTEM10 | AtBAG4 | 6 | 6 |
| S-135 | 18 | TCP97-3388 | pTEM10 | AtBAG4 | 1 | 1 |
| S-135 | 1 | TCP97-3388 | pTEM10 | AtBAG4 | 1 | 1 |
| S-135 | 13 | TCP97-3388 | pTEM10 | AtBAG4 | 5 | 5 |
| S-156 | 4A | CL88-4730 | pTEM10 | AtBAG4 | 4 | 4 |
| S-147 | 15 | TCP97-3388 | pTEM10 | AtBAG4 | NA | NA |
| S-147 | 19 | TCP97-3388 | pTEM10 | AtBAG4 | NA | NA |
| S-147 | 18 | TCP97-3388 | pTEM10 | AtBAG4 | NA | NA |
| S-147 | 23 | TCP97-3388 | pTEM10 | AtBAG4 | NA | NA |
| S-147 | 11 | TCP97-3388 | pTEM10 | AtBAG4 | NA | NA |
| S-175 | 1 | CL88-4730 | pTEM 113 (new BAG4) + pTEM 09 (Ced 9) | AtBAG4 & Ced-9 | NA | NA |
| S-175 | 13 | CL88-4730 | pTEM 113 (new BAG4) + pTEM 09 (Ced 9) | AtBAG4 & Ced-9 | NA | NA |
| S-175 | 15 | CL88-4730 | pTEM 113 (new BAG4) + pTEM 09 (Ced 9) | AtBAG4 & Ced-9 | NA | NA |
| S-175 | 18 | CL88-4730 | pTEM 113 (new BAG4) + pTEM 09 (Ced 9) | AtBAG4 & Ced-9 | NA | NA |
| S-175 | 34 | CL88-4730 | pTEM 113 (new BAG4) + pTEM 09 (Ced 9) | AtBAG4 & Ced-9 | NA | NA |
| S-175 | 2 | CL88-4730 | pTEM 113 (new BAG4) + pTEM 09 (Ced 9) | AtBAG4 & Ced-9 | NA | NA |

TABLE 1-continued

Transformation experiments, transgenes, and sugarcane varieties.

| Transformation Experiment | Plant | Variety | Construct | Transgene | Southern Blot Results Event | Northern Blot Results Event |
|---|---|---|---|---|---|---|
| S-175 | 8 | CL88-4730 | pTEM 113 (new BAG4) + pTEM 09 (Ced 9) | AtBAG4 & Ced-9 | NA | NA |
| S-175 | 11 | CL88-4730 | pTEM 113 (new BAG4) + pTEM 09 (Ced 9) | AtBAG4 & Ced-9 | NA | NA |
| S-175 | 7 | CL88-4730 | pTEM 113 (new BAG4) + pTEM 09 (Ced 9) | AtBAG4 & Ced-9 | NA | NA |
| S-175 | 8 | CL88-4730 | pTEM 113 (new BAG4) + pTEM 09 (Ced 9) | AtBAG4 & Ced-9 | NA | NA |
| S-175 | 10 | CL88-4730 | pTEM 113 (new BAG4) + pTEM 09 (Ced 9) | AtBAG4 & Ced-9 | NA | NA |
| S-175 | 35 | CL88-4730 | pTEM 113 (new BAG4) + pTEM 09 (Ced 9) | AtBAG4 & Ced-9 | NA | NA |
| S-175 | 33 | CL88-4730 | pTEM 113 (new BAG4) + pTEM 09 (Ced 9) | AtBAG4 & Ced-9 | NA | NA |
| S-175 | 20 | CL88-4730 | pTEM 113 (new BAG4) + pTEM 09 (Ced 9) | AtBAG4 & Ced-9 | NA | NA |
| S-175 | 27 | CL88-4730 | pTEM 113 (new BAG4) + pTEM 09 (Ced 9) | AtBAG4 & Ced-9 | NA | NA |
| S-175 | 31 | CL88-4730 | pTEM 113 (new BAG4) + pTEM 09 (Ced 9) | AtBAG4 & Ced-9 | NA | NA |
| S-175 | 24 | CL88-4730 | pTEM 113 (new BAG4) + pTEM 09 (Ced 9) | AtBAG4 & Ced-9 | NA | NA |
| S-175 | 22 | CL88-4730 | pTEM 113 (new BAG4) + pTEM 09 (Ced 9) | AtBAG4 & Ced-9 | NA | NA |
| S-175 | 25 | CL88-4730 | pTEM 113 (new BAG4) + pTEM 09 (Ced 9) | AtBAG4 & Ced-9 | NA | NA |
| S-175 | 36 | CL88-4730 | pTEM 113 (new BAG4) + pTEM 09 (Ced 9) | AtBAG4 & Ced-9 | NA | NA |
| S-175 | 26 | CL88-4730 | pTEM 113 (new BAG4) + pTEM 09 (Ced 9) | AtBAG4 & Ced-9 | NA | NA |
| S-175 | 23 | CL88-4730 | pTEM 113 (new BAG4) + pTEM 09 (Ced 9) | AtBAG4 & Ced-9 | NA | NA |
| S-175 | 21 | CL88-4730 | pTEM 113 (new BAG4) + pTEM 09 (Ced 9) | AtBAG4 & Ced-9 | NA | NA |
| S-175 | 28 | CL88-4730 | pTEM 113 (new BAG4) + pTEM 09 (Ced 9) | AtBAG4 & Ced-9 | NA | NA |
| S-175 | 29 | CL88-4730 | pTEM 113 (new BAG4) + pTEM 09 (Ced 9) | AtBAG4 & Ced-9 | NA | NA |
| S-175 | 9 | CL88-4730 | pTEM 113 (new BAG4) + pTEM 09 (Ced 9) | AtBAG4 & Ced-9 | NA | NA |
| S-175 | 30 | CL88-4730 | pTEM 113 (new BAG4) + pTEM 09 (Ced 9) | AtBAG4 & Ced-9 | NA | NA |
| S-177 | 12 | CP89-2143 | pTEM 113 (new BAG4) + pTEM 09 (Ced 9) | AtBAG4 & Ced-9 | NA | NA |
| S-177 | 16 | CP89-2143 | pTEM 113 (new BAG4) + pTEM 09 (Ced 9) | AtBAG4 & Ced-9 | NA | NA |
| S-177 | 14 | CP89-2143 | pTEM 113 (new BAG4) + pTEM 09 (Ced 9) | AtBAG4 & Ced-9 | NA | NA |

Example 3

Abiotic Stress Tolerance: Transgenic Lines

Figure 2:
FIG. 2 illustrates AtBAG4, Ced-9, and non-transformed plants according to a specific example embodiment of the disclosure.
Figure 3A:
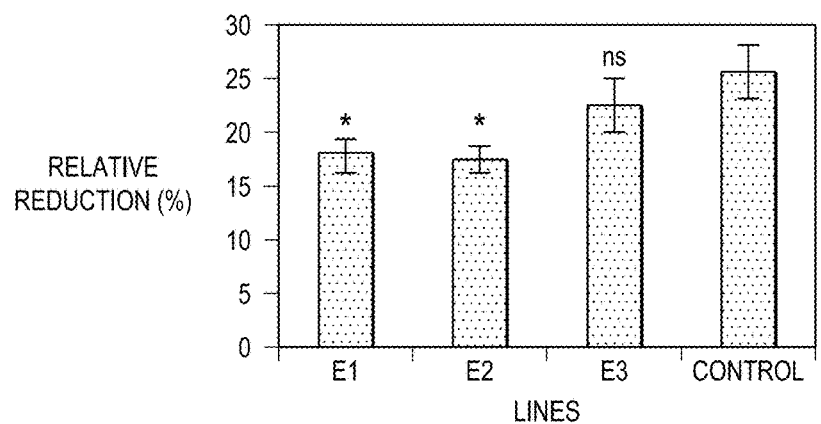
FIG. 3A illustrates drought tolerance data (Fv/Fm) in an AtBAG4 line according to a specific example embodiment of the disclosure.
Figure 3B:
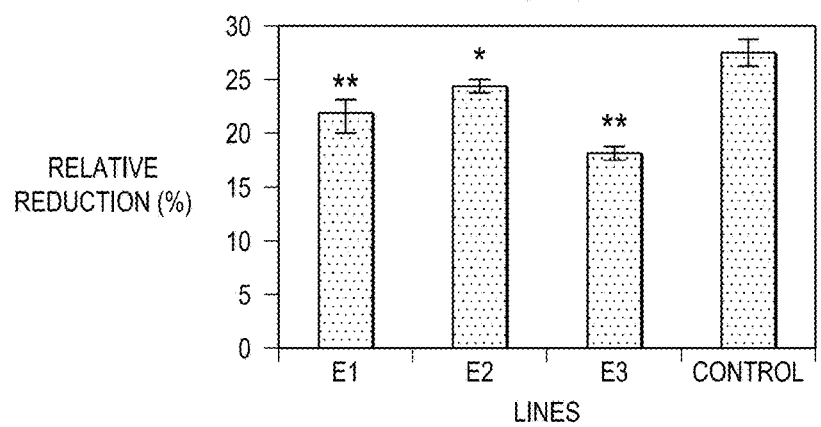
FIG. 3B illustrates drought tolerance data (Relative Water Content) in an AtBAG4 line according to a specific example embodiment of the disclosure.
Figure 3C:
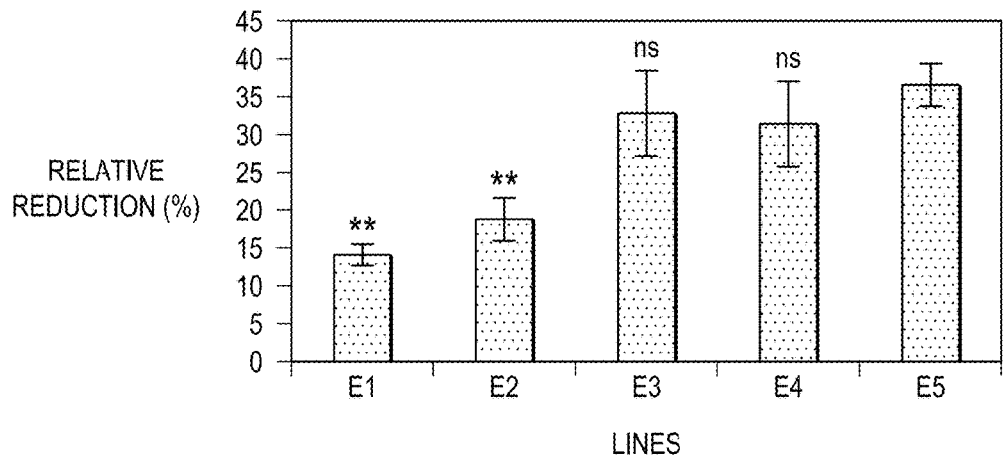
FIG. 3C illustrates drought tolerance data (Fv/Fm) in a Ced-9 line according to a specific example embodiment of the disclosure.
Figure 3D:
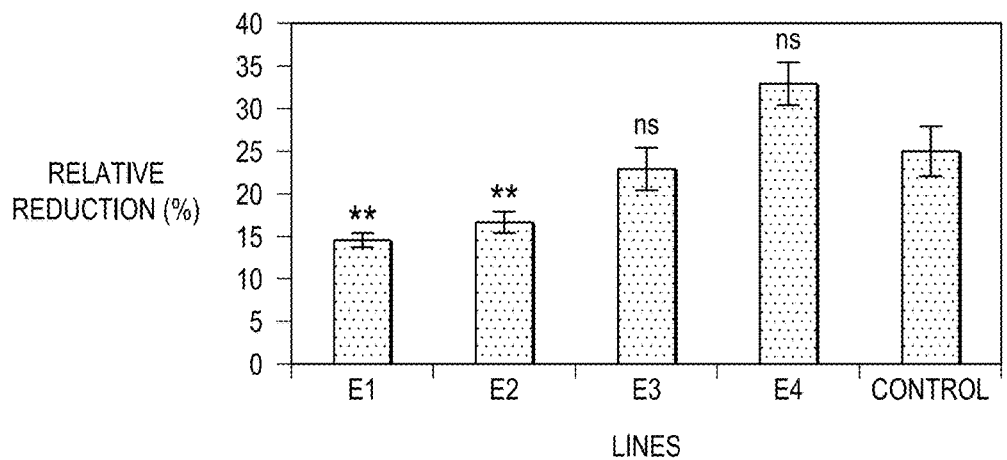
FIG. 3D illustrates drought tolerance data (Relative Water Content) in a Ced-9 line according to a specific example embodiment of the disclosure.

Primary transgenic plants were propagated for stress experiments by single eye stem cuttings (also called setts) and seedlings (FIG. 2) of the first generation transgenic plants. The propagated transgenic plants were then challenged with drought and cold stresses. Control plants, plants that were not transformed with trait or marker genes, were propagated using the same tissue culture and transformation steps as the transgenic plants. FIG. 2 is a photograph illustrating four-week-old second generation seedlings of transgenic plants expressing the trait genes AtBAG4, Ced-9, and non-transformed controls grown under greenhouse conditions. The transgenic sugarcane plants displayed substantially the same growth performance as corresponding wild-type plants.

Example 4

Abiotic Stress Tolerance: Drought

Drought stress experiments were performed using three AtBAG4 events (Events 1, 2 and 3), numerous Ced-9 events, and the corresponding controls. Eight week old sugarcane plants were subjected to a moderately aggressive drought treatment by employing a combination of a bigger pot size and imposing a gradual decrease in the soil moisture level over a longer period of time. Such slow reduction in soil moisture level are intended to mimic the natural drying condition that plants often encounter under field conditions, thereby allowing the plants to deploy drought stress coping mechanisms. Selected drought tolerance indicator traits were measured after 4 weeks of the drought treatment.

As shown in FIG. 3, transgenic plants generated by AtBAG4 events E1, E2, and E3 (FIG. 3A and FIG. 3B) and Ced-9 events E1 and E2 (FIG. 3C and FIG. 3D) exhibited significant drought tolerance as compared to non-transformed controls Data are presented as percent reduction in measured physiological parameters due to drought stress relative to non-stressed controls. FIG. 3A and FIG. 3C show reduction in Fv/Fm in AtBAG4 and Ced-9 lines, respectively, and FIG. 3B and FIG. 3D show reduction in Relative Water Content, in AtBAG4 and Ced-9 lines, respectively. ns, * and ** indicate non significant and significant differences at $p<0.05$ and $p<0.01$, respectively as compared to controls.

The level of drought tolerance conferred varied depending on the specific transformation event. A correlation was observed between improved drought tolerance and increased Ced-9 expression levels. For example, transformation events E1 and E2 have higher expression levels of Ced-9 than events E3 and E4 and displayed better drought tolerance (FIG. 3C and FIG. 3D) than either the lower expressing transformation events or the control. No such correlation was observed in the AtBAG4 transgenic lines.

Example 5

Abiotic Stress Tolerance: Salt Stress

Figure 4A:
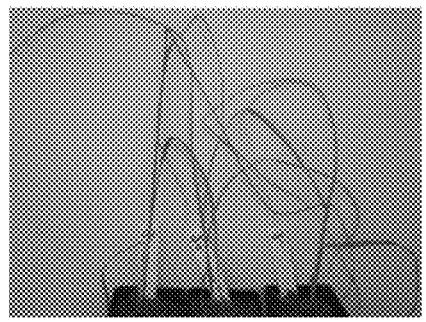
FIG. 4A illustrates salt tolerance results in non-transgenic control plants according to a specific example embodiment of the disclosure.
Figure 4B:
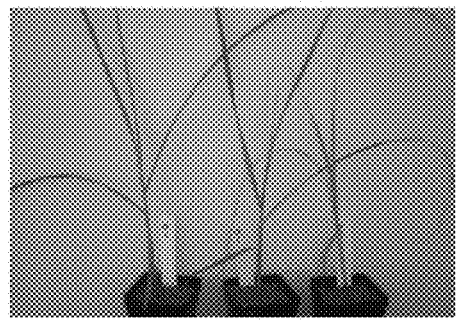
FIG. 4B illustrates salt tolerance results in a transgenic AtBAG4 line (E3) according to a specific example embodiment of the disclosure.
Figure 4C:
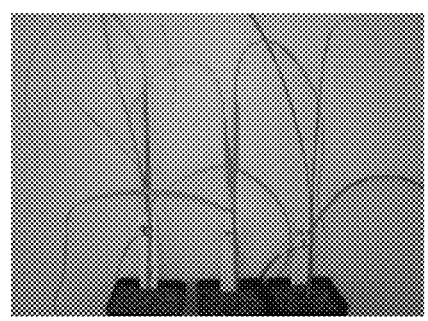
FIG. 4C illustrates salt tolerance results in a transgenic AtBAG4 line (E1) according to a specific example embodiment of the disclosure.

AtBAG4 lines exhibited enhanced salt tolerance compared to control plants. While 70-90% of the AtBAG4 plants survived exposure to very high concentrations of salt (1M NaCl) for 48 h, only 20% of the controls survived this treatment. FIG. 4 illustrates salinity (NaCl) tolerance in transgenic AtBAG4 lines. Five week-old plants of non-transformed (FIG. 4A) and AtBAG4 events E1 (FIG. 4C) and E3 (FIG. 4B) were exposed to high a concentration of salt (1M NaCl) for 48 h. Following the 48 h treatment, the roots were washed to remove the salt and the plants were allowed to grow. Pictures were taken 1 week after removal of the salt stress.

AtBAG4 lines also exhibited increased tolerance to prolonged exposure to salinity. Following over four weeks of exposure to salinity (300 mM NaCl), the AtBAG4 lines had only a 42-44% reduction in total biomass, as compared to non-stressed AtBAG4 plants. By contrast, the non-transgenic, wild type plants exposed to the salinity treatment had a 58% reduction in total biomass when compared to non-stressed wild type controls (data not shown). Similar results were observed when individual organs were evaluated for loss of biomass in response to salinity treatment. For example, the AtBAG4 lines had a 43-46% reduction in shoot dry mass after salinity treatment when compared to non-stressed AtBAG4 plants. By contrast, the non-transgenic, wild-type plants had a 56% reduction in shoot dry mass following salinity treatment when compared to the non-stressed wild type control. Similarly, AtBAG4 lines had only a 32-35% reduction in root dry mass after salinity treatment, while the non-transgenic, wild-type plants exhibited a 64% reduction after treatment.

Example 6

Abiotic Stress Tolerance: Cold Stress

Figure 5:
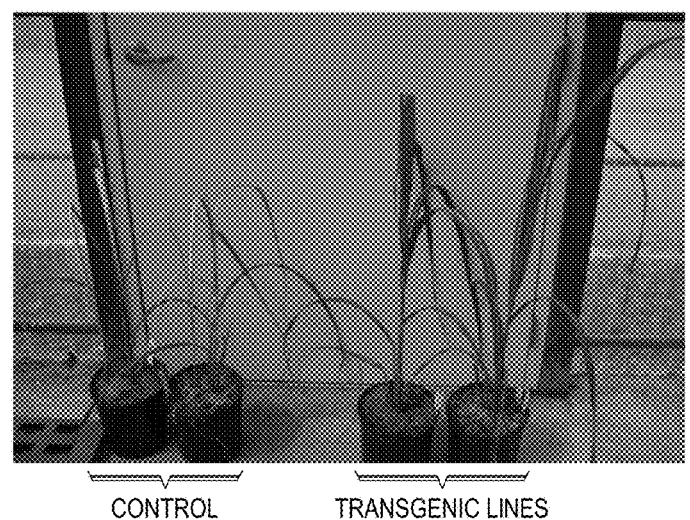
FIG. 5 illustrates cold tolerance results according to a specific example embodiment of the disclosure.

To evaluate plant responses to cold stress, experiments were designed that mimic freezing temperatures experienced outdoors. The treated plants were exposed to 6 hours of freezing temperatures (22° F.) and survival rate was evaluated. Prior to exposure to the freezing temperature, the plants were placed at 45° F. for 24 hours. Initial experiments indicated that when exposed to freezing temperatures AtBAG4 plants had increased survival rates compared to wild type plants. FIG. 5 illustrates non-transgenic control plants (left) and transgenic AtBAG4 expressing plants (right) following exposure to 22° F. for 6 hours. The picture was taken 72 hours after the treatment. Follow up experiments to verify these early results are pending.

Example 7

Other Agronomic Traits: Tillering and Biomass Yield

Figure 6A:
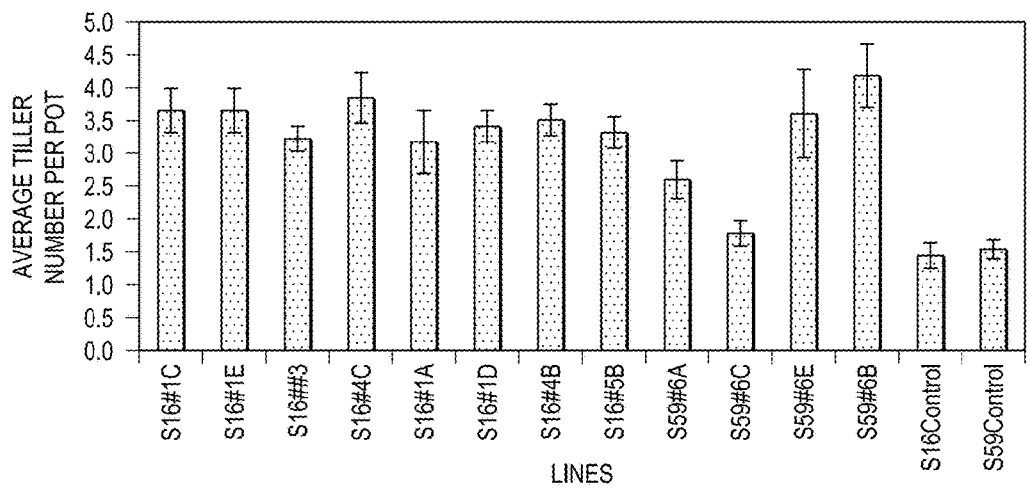
FIG. 6A illustrates tillering performance (average tiller number per pot) in a Ced-9 line according to a specific example embodiment of the disclosure.

Transgenic Ced-9 sugarcane plants displayed enhanced tillering compared to non-transgenic wild type plants when grown in a greenhouse environment (138% increase overall compared to the controls FIG. 6A). This increase in tillering was accompanied by increased cane yield (7-60% higher) in Ced-9 expressing lines compared to the controls (FIG. 6B and FIG. 6C).

Figure 6B:
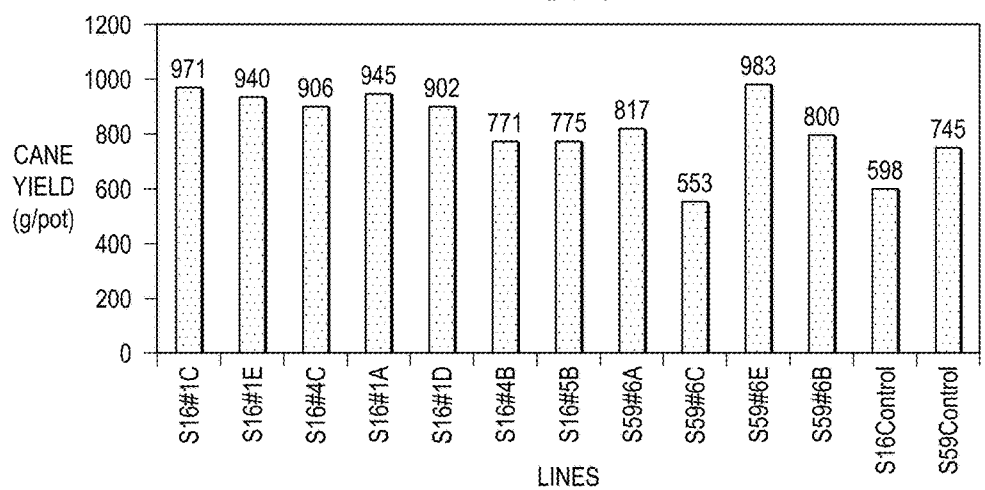
FIG. 6B illustrates cane yield performance in a Ced-9 line according to a specific example embodiment of the disclosure.
Figure 6C:
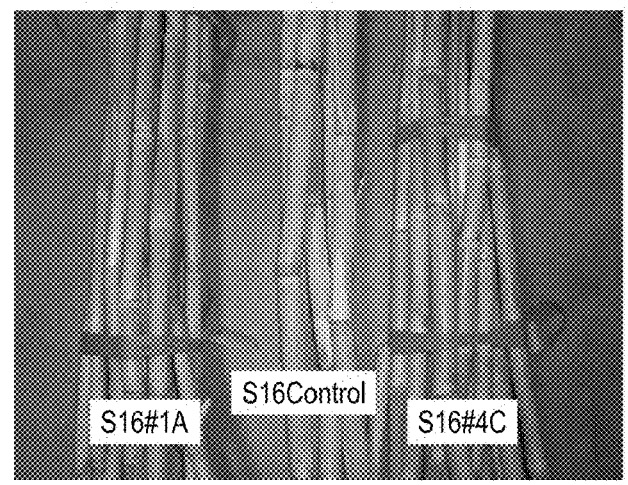
FIG. 6C illustrates yield performance (bundles of cane from 5 pots each) in a Ced-9 line according to a specific example embodiment of the disclosure.

FIG. 6 illustrates enhanced tillering and cane yield in transgenic sugarcane lines expressing Ced-9. FIG. 6A shows average tiller number per pot and FIG. 6B shows cane yield. FIG. 6C shows bundles of cane from 5 pots each of selected sugarcane lines. Plants were harvested four and a half months after planting.

Example 8

Characterization of Plants Transformed by *Agrobacterium*

Table 2 summarizes the *Agrobacterium tumefaciens* mediated transformation experiments performed with different anti-apoptotic genes, as well as, the sugarcane varieties used in each transformation experiment.

TABLE 2

Agrobacterium mediated transformation experiments, transgenes, and sugarcane varieties

| Experiment | Gene | Variety |
|---|---|---|
| Transformation # 1 | YFP | TCP87-3388 |
| Transformation # 2 | YFP | CP72-1210 |
| Transformation # 3 | bcl2-161 and YFP | TCP87-3388 |
| Transformation # 4 | bcl2-161 and YFP | CP72-1210 |
| Transformation # 5 | AtBAG4 and YFP | TCP87-3388 |
| Transformation # 6 | AtBAG4 and YFP | CP72-1210 |
| Transformation # 9 | ced-9 and YFP | CP72-1210 |
| Transformation # 10 | ced-9 and YFP | TCP87-3388 |
| Transformation # 11 | ced-9 and YFP | CP72-1210 |
| Transformation # 12 | ced-9 and YFP | TCP87-3388 |
| Transformation # 13 | ced-9 and YFP | CP72-1210 |
| Transformation # 14 | bcl2-161 and YFP | TCP87-3388 |
| Transformation # 15 | bcl2-161 and YFP | CP72-1210 |
| Transformation # 15.1 | bcl2-161 and YFP | TCP87-3388 |
| Transformation # 20 | Sf-IAP and YFP | CP72-1210 |
| Transformation # 21 | AtBAG4 and YFP | CP72-1210 |
| Transformation # 23 | bcl2-161 and YFP | CP72-1210 |
| Transformation # 26 | ced-9 | TCP98-4454 |

ELISA for the selectable marker nptII (kanamycin resistance) was used as a routine screening method for plants recovered from tissue culture. Approximately 90% of plants growing in the selective medium tested positive using the ELISA screen. Table 3 shows the putative transgenic plants and independent lines recovered from transformation experiments listed in Table 2 that tested positive using the ELISA screen.

TABLE 3

Putative transgenic plants and independent lines recovered from tissue culture and number of experiments performed with each gene.

| Gene | Total Plants | Independent Lines | # Experiments |
|---|---|---|---|
| YFP | 90 | 27 | 7 |
| Control | 165 | 0 | — |
| AtBAG4 | 450 | 39 | 4 |
| ced9(pPTN 261) | 286 | 41 | 6 |
| bcl2-161(pPTN 396) | 539 | 73 | 4 |
| Total | 1530 | 180 | — |

Figure 7:
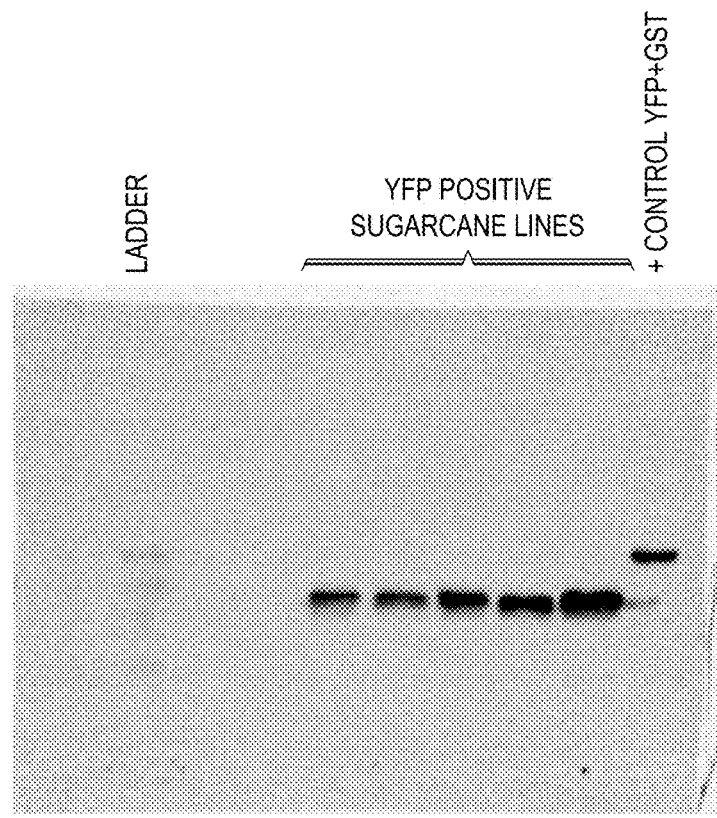
FIG. 7 illustrates a western blot of sugarcane according to a specific example embodiment of the disclosure.
Figure 8:
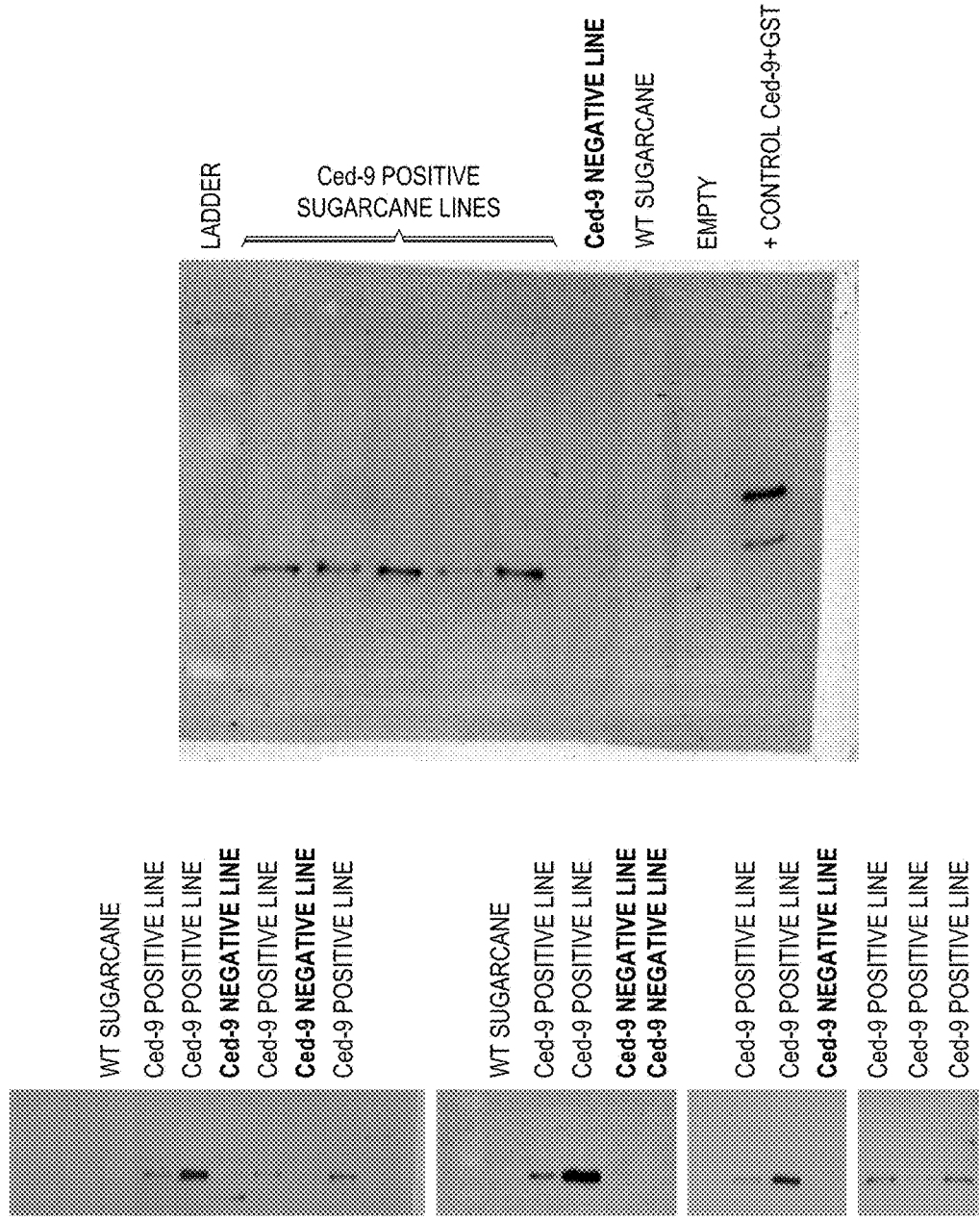
FIG. 8 illustrates western blots of sugarcane according to a specific example embodiment of the disclosure.

Expression of yellow fluorescent protein (YFP) (FIG. 7) and Ced-9 (FIG. 8) protein in transgenic plants have been determined using western Blot analysis. Of the 44 Ced-9 plants that were analyzed, approximately 50% tested positive for the presence of the Ced-9 protein.

Second generation transgenic plants were propagated using stalks from mature plants (~6-8 months in greenhouse after tissue culture process) containing lateral buds. The second generation transgenic plants were propagated under high temperature (~30° C.) and humidity (~80%) conditions. Cold, drought, and salt tolerance experiments were performed using these second generation transgenic plants.

Example 9

Characterization of Plants Transformed by *Agrobacterium*: Stress Tolerance

ELISA positive/DNA blot positive (for presence of transgene and to distinguish individual events) plants were selected for propagation and abiotic stress tolerance evaluation. Second generation transgenic plants were propagated using stalks from mature plants (~6-8 months in greenhouse after tissue culture process) containing lateral buds. The second generation transgenic plants were propagated under high temperature (~30° C.) and humidity (~80%) conditions. Cold, drought, and salt tolerance experiments were performed using these second generation transgenic plants.

All ELISA positive/DNA blot positive transgenic plants recovered (Table 2) from tissue culture (a total of 1530 plants) are in the process of being propagated. Preliminary screening is underway for abiotic stresses tolerance with favorable stress tolerant phenotypes already in hand. Transformation experiments have been successful with the AtBAG4, Ced-9, Bcl2-161 genes using *Agrobacterium* a low copy transformation system.

Example 10

Characterization of Plants Transformed by *Agrobacterium*: Drought Stress

Figure 9:
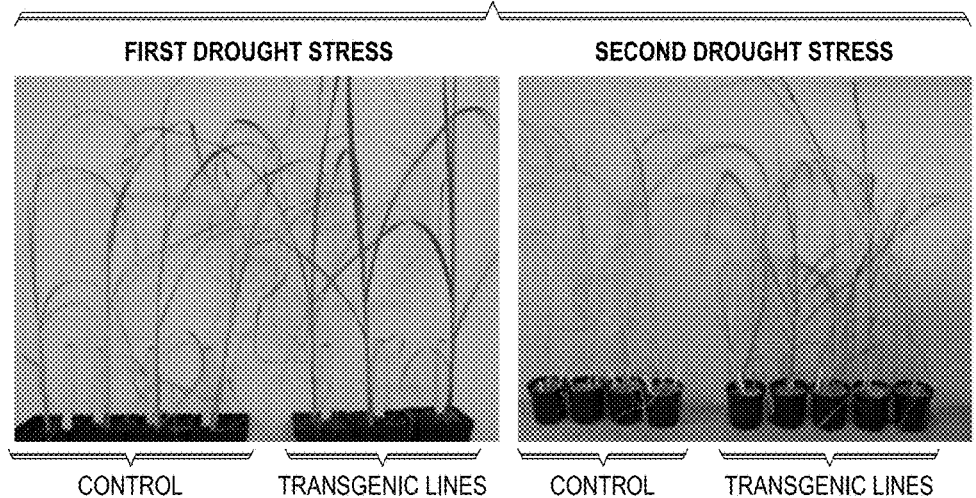
FIG. 9 illustrates drought stress results according to a specific example embodiment of the disclosure.
Figure 10:
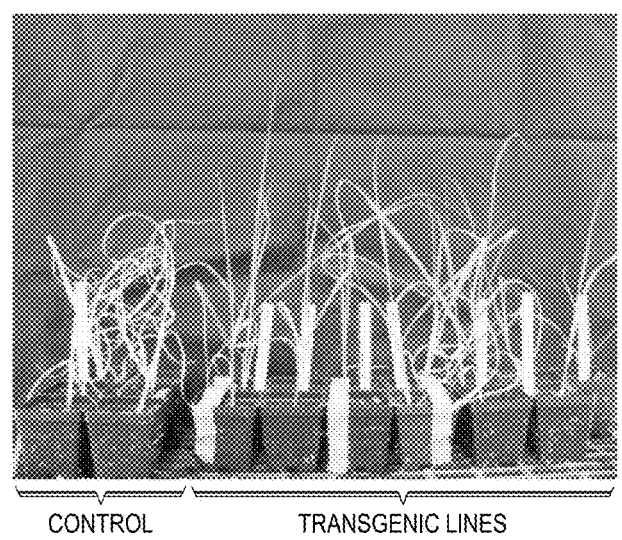
FIG. 10 illustrates drought stress of Bcl2-161 plants according to a specific example embodiment of the disclosure.

Second generation (T2) transgenic lines were evaluated for drought tolerance (see FIG. 9 and FIG. 10). In a first drought stress test (FIG. 9), T2 Ced-9 and AtBAG4 transgenic lines were selected 35-40 days after germination. Drought stress was imposed on the plants by withholding water for 7-10 days. In a second drought stress test, T2 Ced-9 and AtBAG4 transgenic lines were selected 90 days after germination and transferred to larger pots. Drought stress was imposed by withholding water for 17-20 days. The selected drought stress exposure times represent the minimum exposure periods required to obtain irreversible drought stress damage in the wild type control. A plant has irreversible drought stress damage when it cannot recover even after re-hydration. FIG. 9 illustrates the results of a first drought stress test and a second drought stress test using selected Ced-9 and AtBAG4 transgenic lines and a wild type control. The selected transgenic lines remained viable and were not impaired in development in either the first or the second drought stress test. Similar results were observed in the plants in both tests.

FIG. 10 illustrates the results of a drought stress test for selected Bcl2-161 transgenic lines. Bcl2-161 transgenic lines were selected 25-30 days after propagation. Drought stress was imposed by withholding water. The image of FIG. 10 was taken after 12 days without water.

Example 11

Characterization of Plants Transformed by *Agrobacterium*: Salt Tolerance

Additional salt stress experiments were performed under greenhouse conditions wherein plants were watered with a solution of 300 mM NaCl every 5 days for 4 weeks. Under these conditions, several transgenic lines were identified as salt tolerant candidates, while wild type plants showed drastic symptoms of salt stress, (bleaching) and eventual death, initiating in the older leaves and spreading throughout the entire plant (FIG. 11).

FIG. 11 illustrates a salt stress experiment wherein the plants were selected at 25-30 days past germination and subsequently watered every 5 days using a 30 mM NaCl solution. FIG. 11A shows control plants prior to stress treatment. FIG. 11B shows Bcl-2-161 transgenic plants prior to stress treatment. The pictures shown in FIG. 11C were taken 18 days after stress was initiated, with the control plants shown on the left and the Bcl-2-161 transgenic plants shown on the right. In vitro salt stress experiments were performed using plants that were micropropagated using the leaf roll method. Individualized and rooted plants were transferred into a high salt media (150 mM of NaCl) and evaluated after 4 weeks. Under these conditions, several transgenic lines were identified as salt tolerant candidates, while wild type plants showed drastic symptoms of salt stress and posterior death (FIG. 12). FIG. 12 illustrates the results of the in vitro salt stress (150 mM of NaCl) treatment in control plants and AtBAG4 transgenic plants.

Example 12

Characterization of Plants Transformed by Agrobacterium: Cold Stress

Second generation (T2) transgenic lines were evaluated for cold tolerance using T2 plants that were 40 days past germination. The selected plants were maintained at 10° C. for 5 days and then exposed to 0° C. for 20 days. Under these conditions, several transgenic lines were identified as cold tolerant candidates (FIG. 13B, plant on the right), while wild type plants showed drastic symptoms of irreversible cold damage (FIG. 13A; FIG. 13B, plant on left). FIG. 13B illustrates cold tolerance of Ced-9 transgenic plants.

Figure 14A:
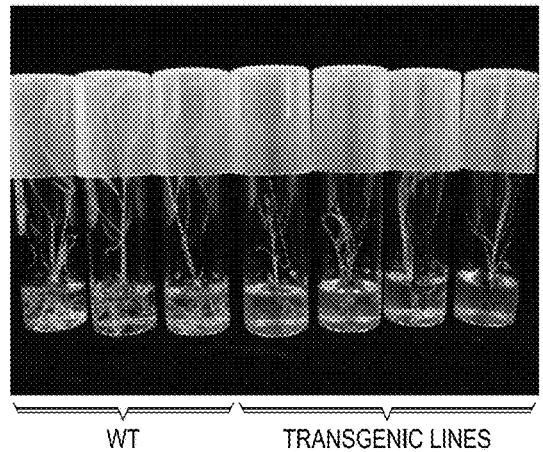
FIG. 14A illustrates results from in vitro 20 minute cold stress experiments in control plants and AtBAG4 transgenic plants according to a specific example embodiment of the disclosure.
Figure 14B:
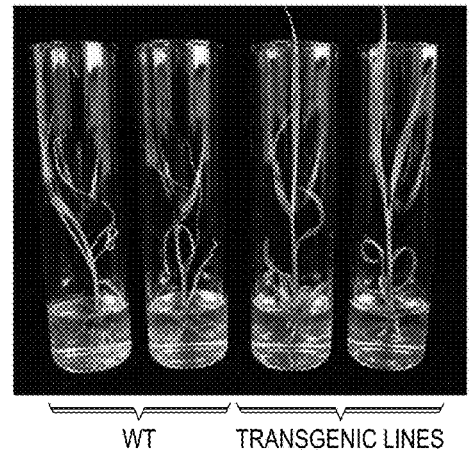
FIG. 14B illustrates results from in vitro 30 minute cold stress experiments in control plants and AtBAG4 transgenic plants according to a specific example embodiment of the disclosure.

Similar results were obtained using in vitro cold stress experiments. Control plants and transgenic lines were micropropagated using the leaf roll method. Individualized and rooted plants were exposed to temperatures of 4° C. for 24 hours, followed by −11° C. for 20 or 30 minutes. Under these conditions, several transgenic lines were identified as cold tolerant candidates, while wild type plants showed drastic symptoms of irreversible cold damage. FIG. 14A shows the results of in vitro 20 minute cold stress experiments using wild type control plants and transgenic AtBAG4 plants. FIG. 14B shows the results of in vitro 30 minute cold stress experiments using wild type control plants and transgenic AtBAG4 plants. The photos in FIG. 14 were taken 10 days after the cold treatment.

Example 13

Characterization of Plants Transformed by Agrobacterium: Heat Stress

Figure 15:
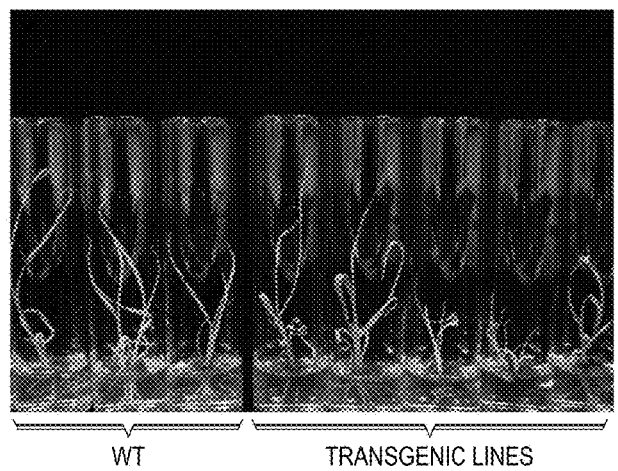
FIG. 15 illustrates heat stress results in control plants and AtBAG4 plants according to a specific example embodiment of the disclosure.

In vitro propagation was used to evaluate the transgenic lines for heat tolerance. Control plants and transgenic lines were micropropagated using the leaf roll method. Individualized and rooted plants were exposed to temperatures of 55° C. for 90 minutes. The plants were evaluated 10 days after the heat treatment and several of the transgenic lines were identified as heat tolerant candidates due to their continued viability. The wild type plants suffered from irreversible heat damage. FIG. 15 illustrates the results of an in vitro heat stress experiment 10 days after treatment with the wild type plants shown on the left and AtBAG4 transgenic lines shown on the right.

Example 14

Characterization of Plants Transformed by Agrobacterium: Multi-location Field Trials of Transgenic Sugarcane AtBAG4 and Ced-9 Events All transgenic sugarcane events and appropriate non-transgenic controls were planted in field trials in College Station, Tex. and in Weslaco, Tex. Propagation materials were also sent to Clewiston, Fla., where they were planted in sandy soil and drought stress conditions.

Around 1000 plants from AtBAG4 and Ced-9 genes were transplanted to an experimental plot located near College Station, Tex. Evaluations were based on plant survival and development during November and December period when the field meteorological tower registered 7 days with freezing temperatures (below 32° F.). Conclusions reached based on experimental data collected are shown in Table 4.

TABLE 4

Figure 16A:
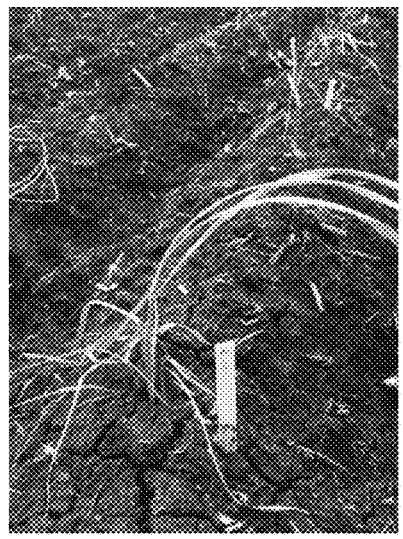
FIG. 16A illustrates cold stress results in control plants according to a specific example embodiment of the disclosure.
Figure 16B:
FIG. 16B illustrates cold stress results in AtBAG4 plants according to a specific example embodiment of the disclosure.
Figure 17A:
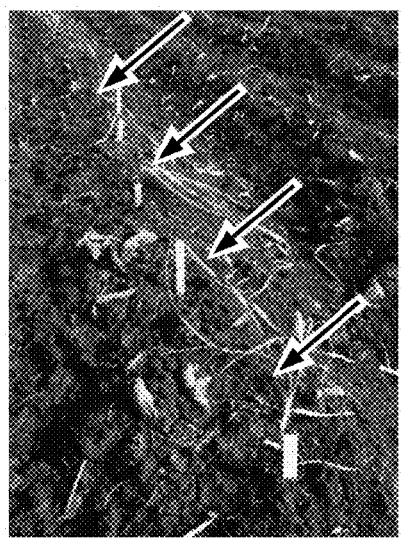
FIG. 17A illustrates wild type sugarcane plants afflicted with irreversible cold damage according to a specific example embodiment of the disclosure.
Figure 17B:
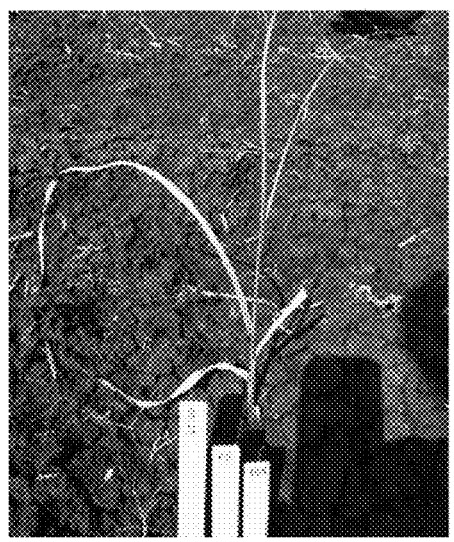
FIG. 17B illustrates cold tolerance of Ced-9 transgenic plants according to a specific example embodiment of the disclosure.

| Field test observations |
| --- |
| AtBAG4 Experiment |
| 30% of the initial transgenic lines survived the applied cold stress (FIG. 16B, showing an AtBAG4 plant) |
| 98% of the wild type controls did not survive the applied cold stress (FIG. 16A) |
| Ced-9 Experiment |
| 63% of the initial transgenic lines survived the applied cold stress (FIG. 17B) |
| 100% of the wild type controls did not survive the applied cold stress (FIG. 17A) |

The aerial portions of all plants, wild-type controls and transgenic lines, were killed during a 4-day long freeze in January. The following spring 30% of the transgenic plants re-grew, while none of the controls re-grew.

Example 15

Characterization of Plants Transformed by Agrobacterium: Ced-9

Embryogenic calli of sugarcane (Sacharum officinarum L.) genotypes TCP87-3388 and CP72-1210 were transformed with the anti-apoptotic gene Ced-9, a C. elegans homolog of the mammalian Bcl-2 cytoprotective gene family. Transformed plants were selected on culture medium containing Geneticin, and characterized by ELISA for the presence of nptII protein. T2 transgenic lines were evaluated for drought tolerance at two different developmental stages; 40 and 90 days post germination, with water deprivation periods of 10 and 20 days, respectively. Candidate drought tolerant plants were recovered in both tests. The selected deprivation water periods represent the minimum amount of time after which wild type plants were unable to recover (even after rehydration). Selected transgenic lines remained viable and were not impaired in development. These results suggest that the anti-apoptotic gene Ced-9 integrated into the genome of sugarcane may confer drought tolerance. Further experiments are underway to investigate the role of Ced-9 in other abiotic stresses, including salt, cold and heat.

Example 16

Characterization of Biolistically Transformed-Plants: AtBAG4 and Ced-9

Field test data were collected for biolistically transformed sugarcane plants with native AtBAG4 and Ced-9 events. The field plot consisted of 20 feet of each transformation event. One year after planting, 10 stalks were randomly selected from each plot. The plants tested were all of the same variety, CP72-1210, which accounts for the majority of the acreage in Texas. The selected stalks were weighed and sucrose purity and yield were determined. A standard juice analysis, commonly used by sugarcane breeders to make their best selections, was performed. The resulting data shows that the expression of the AtBAG4 and Ced-9 genes-does not diminish sugar yields.

Table 5 illustrates the results of further sugar yield studies using field trials consisting of 75 foot plots of transformed sugarcane plants with AtBAG4 and Ced-9 events. Each plot was replicated three times. Table 5 includes data reflecting purity, fiber content, ash content (potassium), tons of cane per acre (TCA), tons of sugar per acre (TSA) and pounds of sugar per acre (lbs). The purity of the sugarcane sample was evaluated using a standard juice analysis. The data reflects the percent of sucrose contained within the juice. The fiber content of the canes was analyzed using a standard assay.

The AtBAG4 and Ced-9 transformants did not show significant decreases in sugar yield as compared to the wild type.

binary vector and cloned into HindIII/EcoRI site of pBluescript to generate Ubi::AtBAG4::NOS/pSK+. Each of these vectors was used to transform sugarcane together with a plant selectable marker Ubi::BAR::NOS/pSK+.

Figure 18:
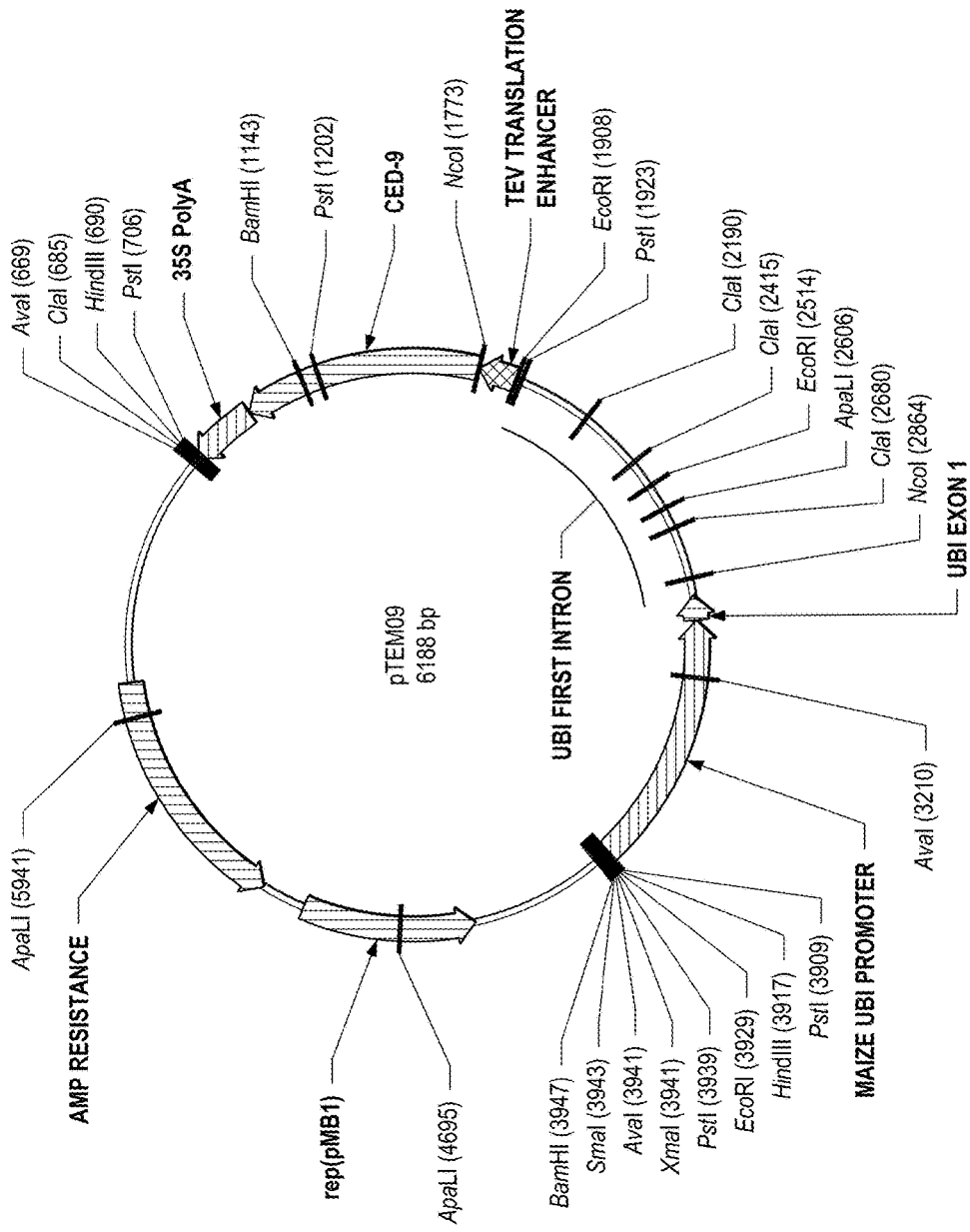
FIG. 18 illustrates expression vector pTEM09 according to a specific example embodiment of the disclosure.

Expression vectors were prepared for biolistic bombardment with AtBAG4 and *C. elegans* Ced-9 sequences. Briefly, the sequences for AtBAG4 (SEQ ID NO: 1) and Ced-9 (SEQ ID NO: 3) were adapted for expression in sugarcane by replacing the native 5' and 3' untranslated regions (UTRs) with the Nos Terminator for the 3' UTR and the Mazie Ubi 5' UTR in the constructs. The AtBAG4 sequence was further modified by codon optimization for expression in sugarcane using sorghum genome sequence information and a proprietary algorithm made available from GeneScript. FIG. 18 and SEQ ID NO: 5 illustrate a pTEM09-based expression vector and cassette, respectively,

TABLE 5

Sugar yields from field trials consisting of AtBAG4 and Ced-9 sugarcane transformation events

| Lines/Events | JUICE % PURITY | CANE % FIBER | ASH | TCA | TSA | SUGAR/AC. lbs. |
|---|---|---|---|---|---|---|
| S12 9A2 | 83.05 | 14.27 | 273.67 | 40.66 | 3.64 | 7289.43 |
| S12 9C | 82.67 | 14.17 | 282.67 | 42.20 | 3.64 | 7287.49 |
| S12 CONTROL | 79.98 | 12.97 | 263.00 | 42.98 | 3.61 | 7211.21 |
| S12 17-1 | 81.38 | 14.66 | 250.50 | 42.98 | 3.60 | 7199.02 |
| S12 9D | 80.64 | 14.53 | 254.50 | 42.40 | 3.47 | 6938.82 |
| S12 17-4 | 80.24 | 13.90 | 258.50 | 42.40 | 3.45 | 6895.26 |
| S12 18 | 81.70 | 14.15 | 279.50 | 40.95 | 3.43 | 6858.38 |
| S12 11C | 81.22 | 12.90 | 267.67 | 37.95 | 3.27 | 6539.81 |
| S16 CONTROL | 80.51 | 14.74 | 275.00 | 39.49 | 3.19 | 6380.67 |
| S16 1C | 80.18 | 13.63 | 258.33 | 37.95 | 3.14 | 6287.35 |
| S59 6A | 80.57 | 13.73 | 223.33 | 36.78 | 3.13 | 6269.16 |
| S59 CONTROL2 | 81.96 | 11.76 | 211.00 | 34.85 | 3.10 | 6202.94 |
| S16 1E | 80.57 | 13.84 | 247.00 | 36.01 | 2.99 | 5983.40 |
| S12 17-3 | 80.12 | 17.00 | 295.00 | 40.66 | 2.99 | 5976.43 |
| S12 1D | 81.33 | 13.74 | 262.33 | 36.01 | 2.98 | 5955.14 |
| S16 5B | 79.57 | 13.53 | 252.50 | 33.98 | 2.84 | 5676.16 |
| S12 3 | 80.81 | 13.73 | 268.00 | 33.98 | 2.75 | 5501.19 |
| S16 4B | 80.05 | 13.88 | 249.50 | 35.43 | 2.71 | 5422.64 |
| S12 1C | 79.97 | 14.57 | 266.67 | 34.85 | 2.69 | 5373.56 |
| S59 6B | 80.68 | 12.48 | 243.33 | 31.36 | 2.68 | 5363.11 |
| S12 18-2 | 79.40 | 12.90 | 250.33 | 33.30 | 2.65 | 5303.48 |
| S16 3 | 82.47 | 17.59 | 216.00 | 30.20 | 2.61 | 5224.88 |
| S59 6C | 81.30 | 15.32 | 271.33 | 32.14 | 2.58 | 5153.63 |
| S12 6B | 79.95 | 13.01 | 242.50 | 31.36 | 2.45 | 4892.66 |
| S16 1A | 80.42 | 15.20 | 281.50 | 31.07 | 2.37 | 4733.52 |
| S16 4C | 78.46 | 13.68 | 258.75 | 30.20 | 2.17 | 4333.06 |
| S16 1D | 80.71 | 13.82 | 274.00 | 27.88 | 2.15 | 4300.24 |
| S59 CONTROL | 79.95 | 13.22 | 259.67 | 27.10 | 2.12 | 4234.81 |
| S59 6E | 81.92 | 14.14 | 263.00 | 15.10 | 1.27 | 2536.93 |
| Mean | 80.75 | 14.04 | 258.59 | 35.25 | 2.88 | 5769.81 |
| SD | 1.03 | 1.19 | 19.15 | 6.09 | 0.56 | 1112.23 |
| CV % | 1.27 | 8.51 | 7.41 | 17.29 | 19.28 | 19.28 |
| LSD | 0.000 | 0.000 | 0.000 | 0.000 | 0.000 | 0.000 |

SD reflects the standard deviation.
CV % reflects the confidence value.
LSD refers to the least significant difference.

Example 17

Vectors for Biolistic Transformation of Sugarcane

Figure 19:
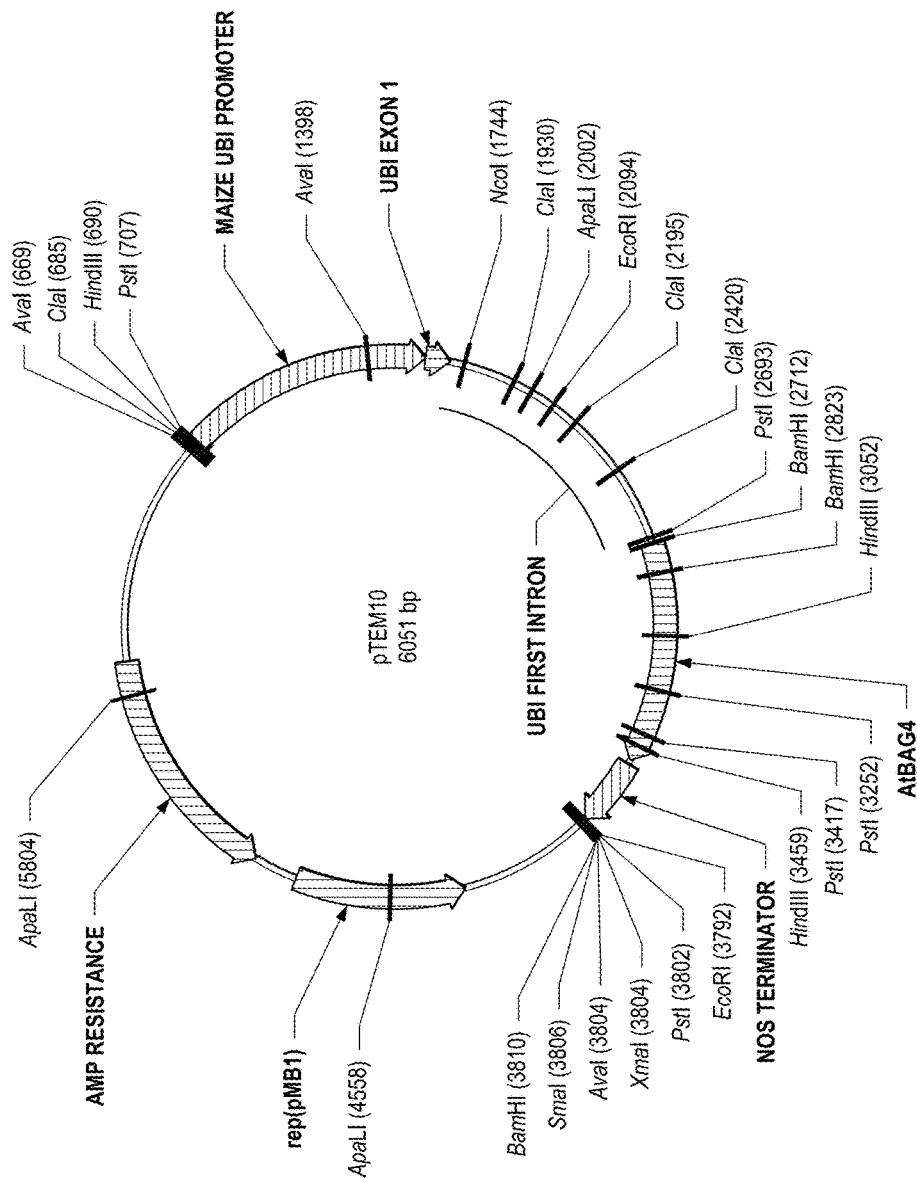
FIG. 19 illustrates expression vector pTEM10 according to a specific example embodiment of the disclosure.
Figure 21:
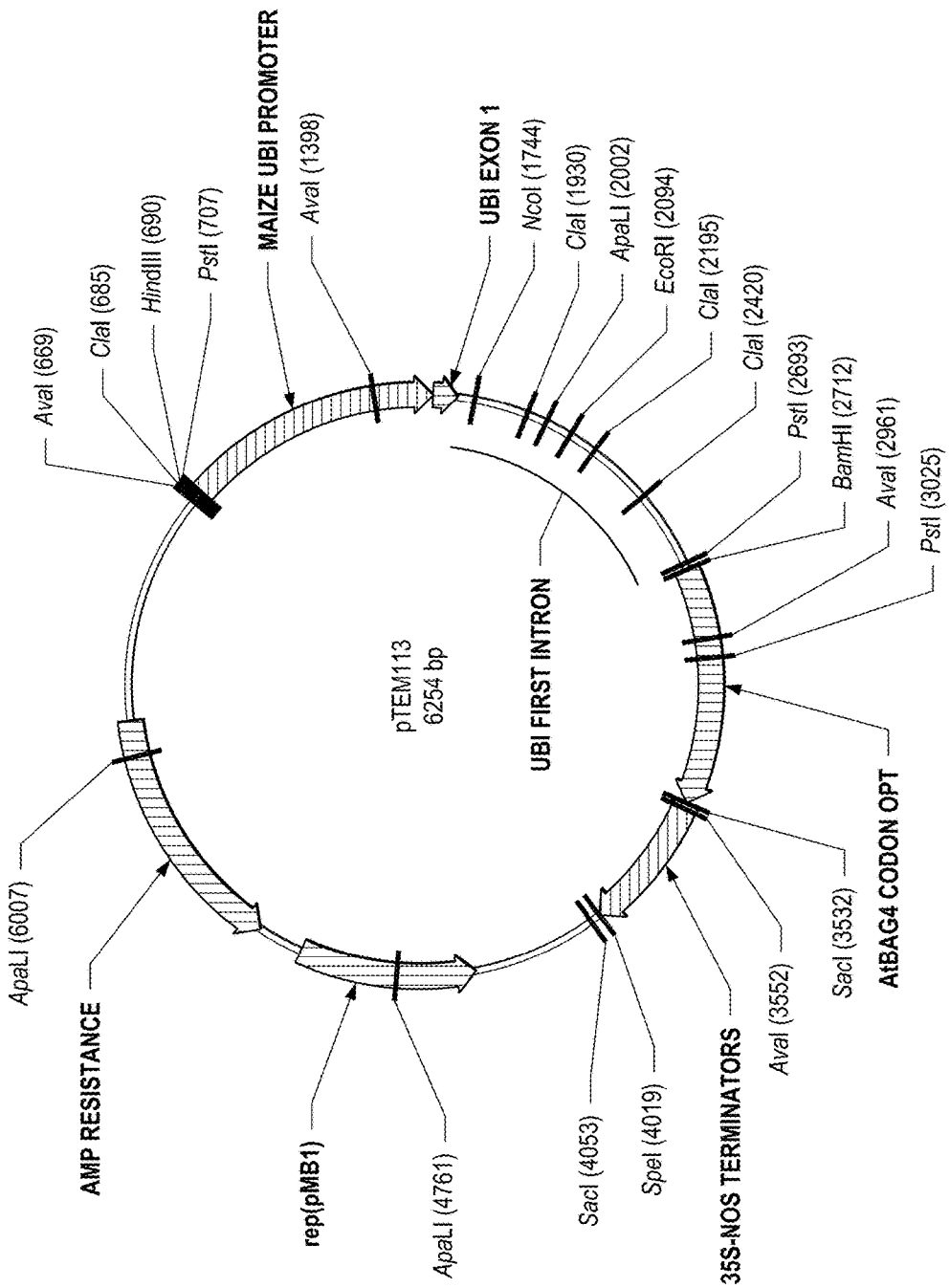
FIG. 21 illustrates expression vector pTEM113 according to a specific example embodiment of the disclosure.

Binary vectors pPTN261 and pPTN-AtBAG4 harboring plant expression cassettes for Ced-9 and AtBAG4 genes were generated. To generate handy vectors for biolistic transformation, the Ced-9 expression cassette (Ubi::Ced9::35 ST) was released from pPTN261 by single digest with HindIII and sub-cloned into HindIII site of pBlusscript SK+ to generate Ubi::Ced9::35 ST/pSK+. The AtBAG4 expression cassette, (Ubi::AtBAG4::NOS) was obtained as HindIII/NcoI and NcoI/EcoRI fragments from pPTN-AtBAG4 comprising Ced-9. FIG. 19 and SEQ ID NO: 6 illustrate a pTEM10-based expression vector and cassette, respectively, comprising native AtBAG4. FIG. 21 and SEQ ID NO: 7 illustrate an expression vector and cassette, respectively, comprising codon-optimized AtBAG4.

Example 18

Biolistic Transformation of Sugarcane

For sugarcane transformation, embryogenic callus cultures were established from young leaf bases and immature flowers of sugarcane (*Saccharum* spp. hybrid) (Beyene et al., 2011, *Plant Cell Rep* 30:13-25) cultivars CP72-1210, TCP98-4454, TCP87-3388 and L97-128. Transformation of callus by DNA particle gun bombardment, using tungsten or gold (Bio-Rad Laboratories, CA), as well as regeneration of shoots and roots were essentially performed as described previously (Gallo-Meagher and Irvine, 1996, *Plant Cell Reporter* 12:666-670; Beyene et al., 2011). Briefly, about eight week-old embryogenic calli were bombarded with the desired plasmid DNA (2 µg DNA/480 µg particles) and maintained on MS3 medium for seven days in the dark at 28° C. for recovery. Bombarded calli were later broken into small pieces and incubated in the dark at 28° C. on callus induction medium, MS3 with 2,4-D (3 mg per L) and bialaphos (3 mg per L) or geneticin (G418) (15 mg per L) selection, for a period of one month. For shoot regeneration, calli were grown on MS supplemented with BAP (2 mg per L) and bialaphos (3 mg per L) or geneticin (15 mg per L) for six to eight weeks under a light (16 h)/dark (8 h) photoperiod. Green shoots of approximately 2 cm in height were transferred into MS rooting medium containing indole-3-butyric acid (4 mg per L) and bialaphos (4 mg per L) or geneticin (15 mg per L). Rooted plantlets were transferred to potting soil (Metromix) in small pots, maintained in an environmental growth chamber at 30° C. under 15 hours of fluorescent and incandescent light for two weeks, and transferred to the greenhouse in 15 cm-diameter pots at 30° C. under natural sunlight.

Example 19

Vectors for Transformation of Sugarcane with *Agrobacterium*

Figure 20:
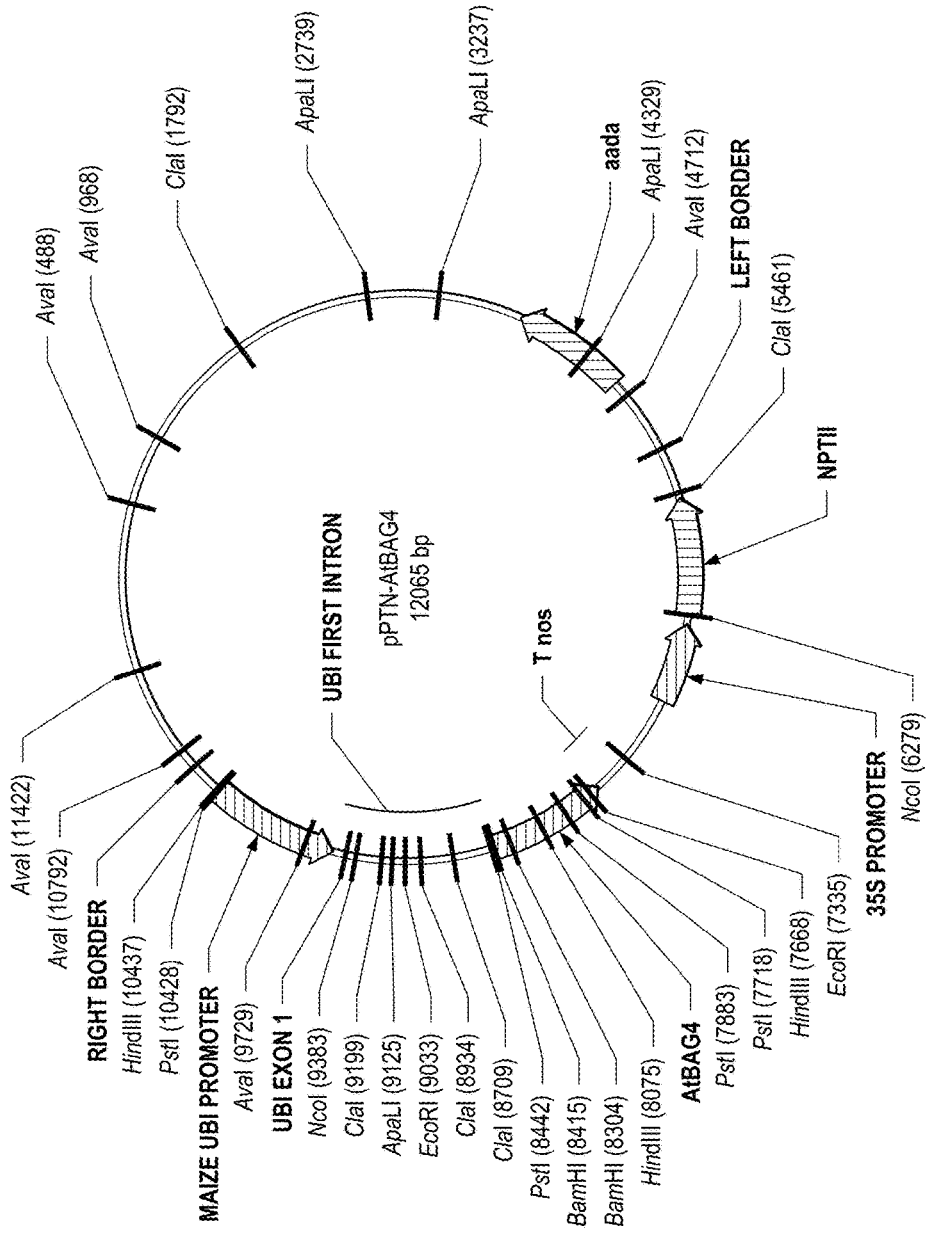
FIG. 20 illustrates expression vector pPTN-AtBAG4 according to a specific example embodiment of the disclosure.
Figure 22:
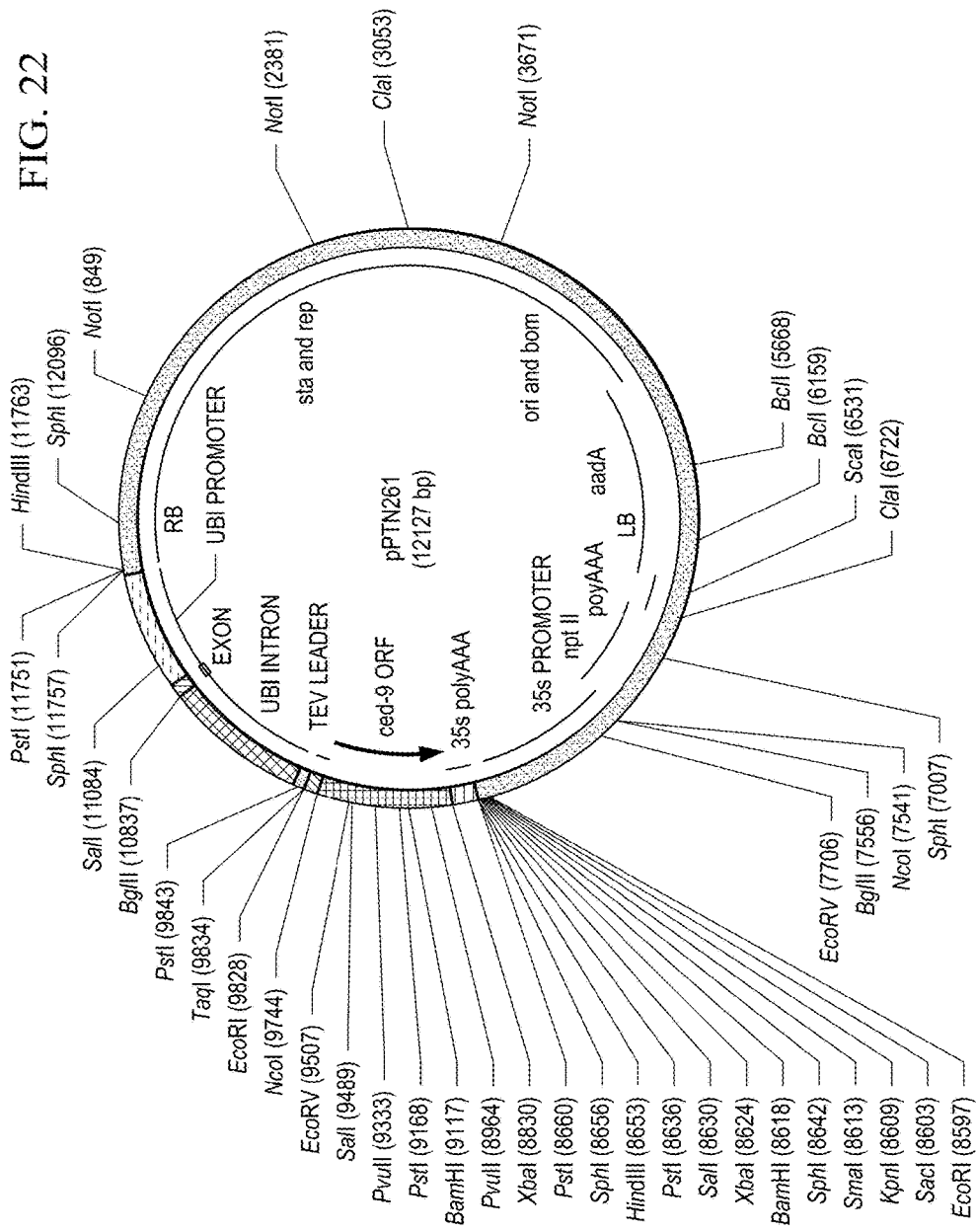
FIG. 22 illustrates expression vector pPTN261 according to a specific example embodiment of the disclosure.
Figure 23:
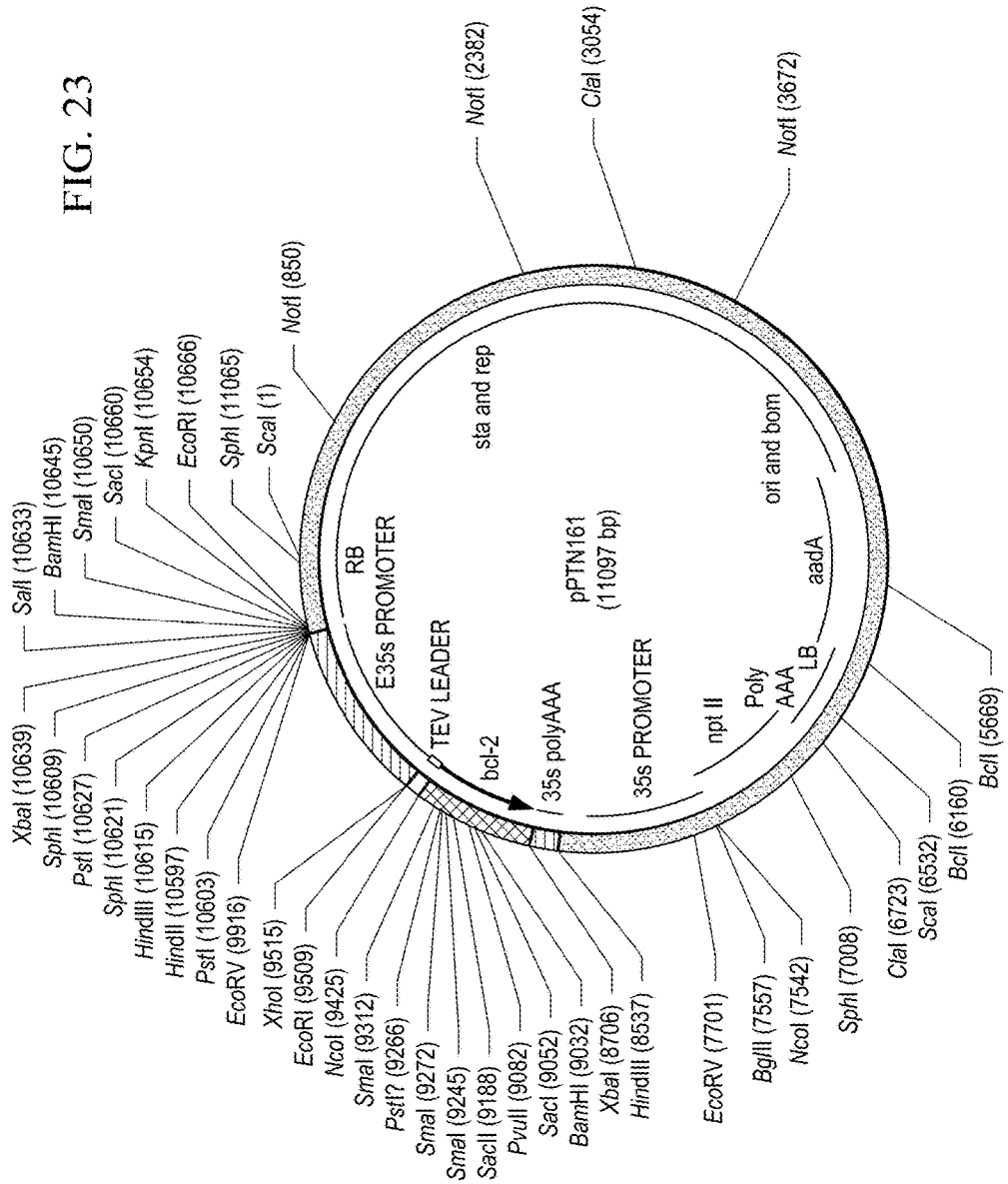
FIG. 23 illustrates expression vector pPTN161 according to a specific example embodiment of the disclosure.
Figure 24:
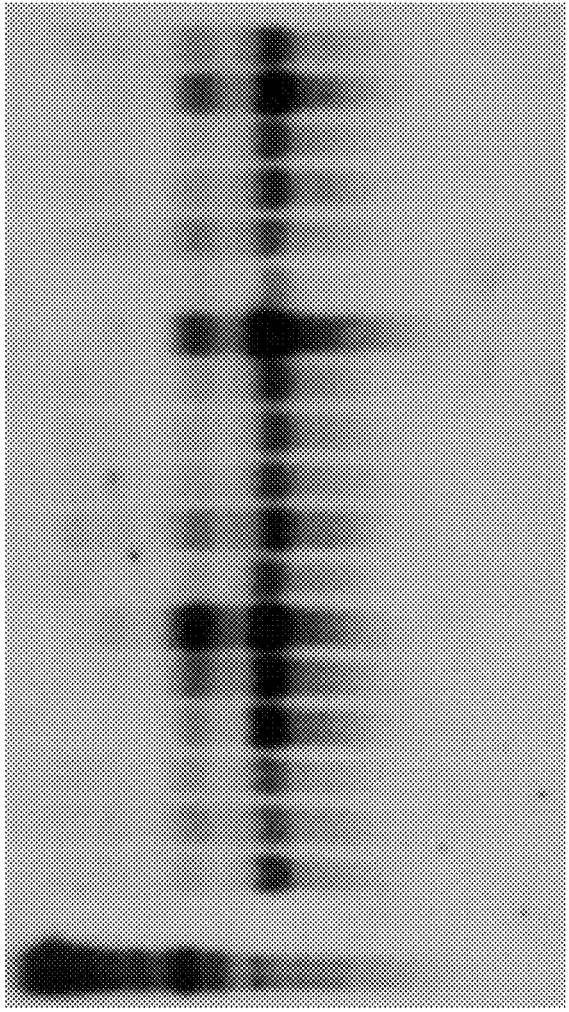
FIG. 24 illustrates a northern blot of sugarcane plants expressing AtBAG4 according to a specific example embodiment of the disclosure.

Expression Vectors were prepared for biolistic bombardment with AtBAG4 and *C. elegans* Ced-9 sequences. FIG. 20 illustrates a pPTN-based expression vector and cassette, respectively, comprising AtBAG4. FIG. 22 illustrates a pPTN261-based expression vector comprising Ced-9. SEQ ID NO: 8 illustrates an expression cassette comprising an AtBAG4. FIG. 23 illustrates a pPTN161-based expression vector comprising human Bcl-2-161.

Example 20

Transformation of Sugarcane with *Agrobacterium*

*Agrobacterium*-mediated transformation of sugarcane was carried out generally as described by Joyce et al. (Plant Cell Reports, 2010, 29(2):173-183).

What is claimed is:

1. A sugarcane plant characterized by displaying an improved abiotic stress tolerance over a corresponding wild-type plant, the sugarcane plant comprising:
   an expression control sequence operable in the host; and
   an expressible nucleic acid sequence encoding the amino acid sequence of SEQ ID NO: 2operably linked to the expression control sequence,
   wherein the expressible nucleic acid sequence is nucleotides 2016-2825 of SEQ ID NO: 7, and
   wherein the expression control sequence is constitutively expressed, and
   wherein the improved abiotic stress tolerance is selected from the group consisting of improved cold tolerance, improved drought tolerance, improved heat tolerance, improved salt tolerance, and combinations thereof.

2. The sugarcane plant according to claim 1, wherein the plant has substantially the same stem height, leaf area, dry mass, sugar content, and/or days to flowering as the corresponding wild-type plant when both are cultivated under the same greenhouse conditions.

3. The sugarcane plant according to claim 1, wherein the expression control sequence comprises a ubiquitin promoter or a cauliflower mosaic virus 35S promoter.

4. A method of producing sugarcane characterized by displaying an improved abiotic stress tolerance over corresponding wild-type plants, the method comprising:
   contacting a sugarcane plant cell with a nucleic acid under conditions that permit incorporation of at least a portion of the nucleic acid into the host genome; and
   regenerating a plant from the contacted plant cell,
   wherein the plant comprises the incorporated nucleic acid,
   wherein the incorporated nucleic acid comprises an expression control sequence operable in the host, and an expressible nucleic acid sequence encoding an amino acid sequence of SEQ ID NO: 2 operably linked to the expression control sequence,
   wherein the nucleic acid sequence of the nucleic acid is nucleotides 2016-2825 of SEQ ID NO: 7,
   wherein the expression control sequence is constitutively expressed, and
   wherein the improved abiotic stress tolerance is selected from the group consisting of improved cold tolerance, improved drought tolerance, improved heat tolerance, improved salt tolerance, and combinations thereof.

5. The method according to claim 4, wherein the regenerated transgenic plant has substantially the same stem height, leaf area, dry mass, sugar content, and/or days to flowering as the corresponding wild-type plant when both are cultivated under the same greenhouse conditions.

6. The method according to claim 4, wherein the expression control sequence comprises a ubiquitin promoter or a cauliflower mosaic virus 35S promoter.

7. An expression cassette or expression vector for improving an abiotic stress tolerance in a sugarcane plant, the expression cassette or expression vector comprising, in a 5' to 3' direction:
   an expression control sequence operable in the sugarcane host plant;
   a nucleic acid sequence that encodes an amino acid sequence of SEQ ID NO: 2; and
   a terminator operable in in the sugarcane host plant,
   wherein the nucleic acid sequence of the nucleic acid is nucleotides 2016-2825 of SEQ ID NO: 7,
   wherein the expression control sequence is constitutively expressed, and
   wherein the improved abiotic stress tolerance is selected from the group consisting of improved cold tolerance, improved drought tolerance, improved heat tolerance, improved salt tolerance, and combinations thereof.

8. The expression cassette or expression vector according to claim 7, wherein the expression control sequence comprises a ubiquitin promoter or a cauliflower mosaic virus 35S promoter.

9. The expression cassette or expression vector according to claim 7, wherein the terminator comprises a 35S terminator and/or a NOS terminator.

10. A microorganism for improving abiotic stress tolerance in a sugarcane plant, the microorganism comprising:
    an expression cassette or expression vector comprising, in a 5' to 3' direction:
    an expression control sequence operable in the sugarcane host plant;
    a nucleic acid sequence that encodes an amino acid sequence of SEQ ID NO: 2; and
    a terminator operable in in the sugarcane host plant,
    wherein the nucleic acid sequence of the nucleic acid is nucleotides 2016-2825 of SEQ ID NO: 7,
    wherein the expression control sequence is constitutively expressed, and
    wherein the improved abiotic stress tolerance is selected from the group consisting of improved cold tolerance, improved drought tolerance, improved heat tolerance, improved salt tolerance, and combinations thereof.

11. The microorganism according to claim 10, wherein the expression control sequence comprises a ubiquitin promoter or a cauliflower mosaic virus 35S promoter.

12. The microorganism according to claim 10, wherein the terminator is selected from a 35S terminator, a NOS terminator, and a combination thereof.

* * * * *